US010962404B2

(12) United States Patent
Kamiyama et al.

(10) Patent No.: US 10,962,404 B2
(45) Date of Patent: Mar. 30, 2021

(54) SYSTEMS AND METHODS FOR WEIGHT MEASUREMENT FROM USER PHOTOS USING DEEP LEARNING NETWORKS

(71) Applicant: Bodygram, Inc., Las Vegas, NV (US)

(72) Inventors: Kyohei Kamiyama, Tokyo (JP); Chong Jin Koh, Las Vegas, NV (US); Yu Sato, Kawasaki (JP)

(73) Assignee: Bodygram, Inc., Las Vegas, NV (US)

( * ) Notice: Subject to any disclaimer, the term of this patent is extended or adjusted under 35 U.S.C. 154(b) by 0 days.

(21) Appl. No.: 16/830,497

(22) Filed: Mar. 26, 2020

(65) Prior Publication Data

US 2020/0319015 A1    Oct. 8, 2020

Related U.S. Application Data

(60) Provisional application No. 62/828,373, filed on Apr. 2, 2019.

(51) Int. Cl.
| | |
|---|---|
| G06K 9/00 | (2006.01) |
| G01G 19/44 | (2006.01) |
| G06N 20/00 | (2019.01) |
| A61B 5/11 | (2006.01) |
| G06T 7/62 | (2017.01) |
| A61B 5/107 | (2006.01) |

(52) U.S. Cl.
CPC .......... *G01G 19/44* (2013.01); *A61B 5/1075* (2013.01); *A61B 5/1128* (2013.01); *G06K 9/00369* (2013.01); *G06N 20/00* (2019.01); *G06T 7/62* (2017.01)

(58) Field of Classification Search
CPC ...................................................... G01G 19/44
See application file for complete search history.

(56) References Cited

U.S. PATENT DOCUMENTS

| | | | |
|---|---|---|---|
| 10,026,187 B2 | 7/2018 | McCloskey et al. | |
| 10,282,914 B1* | 5/2019 | Tran | A61B 5/1128 |
| 2010/0111370 A1* | 5/2010 | Black | G06K 9/00369 382/111 |
| 2019/0108667 A1* | 4/2019 | Streuber | G06T 13/40 |

(Continued)

OTHER PUBLICATIONS

Biggs. "Original Stitch's new bodygram will measure your body" TechCrunch, Jul. 2, 2018 (Year: 2018).*

(Continued)

*Primary Examiner* — Oneal R Mistry
(74) *Attorney, Agent, or Firm* — American Patent Agency PC; Daniar Hussain; Xiaomeng Shi

(57) ABSTRACT

Disclosed are systems and methods for body weight prediction from one or more images. The method includes the steps of receiving one or more subject parameters; receiving one or more images containing a subject; identifying one or more annotation key points for one or more body features underneath a clothing of the subject from the one or more images utilizing one or more annotation deep-learning networks; calculating one or more geometric features of the subject based on the one or more annotation key points; and generating a prediction of the body weight of the subject utilizing a weight machine-learning module based on the one or more geometric features of the subject and the one or more subject parameters.

20 Claims, 11 Drawing Sheets

(56) References Cited

U.S. PATENT DOCUMENTS

2020/0051565 A1* 2/2020 Singh .................... G10L 13/043
2020/0126295 A1* 4/2020 Mok ....................... G06T 17/20

OTHER PUBLICATIONS

Biggs et al NPL "Original Stitch's new Body Measure your body", Jul. 2, 2018, (Year: 2018).*

Antitza Dantcheva, François Bremond, Piotr Bilinski. "Show me your face and I will tell you your height, weight and body mass index." International Coference on Pattern Recognition (ICPR), Aug. 2018, Beijing, China. ffhal-01799574f.

Beef Central, "Smartphone accessory calculates cattle weights from metres away + Video", Beef Central, Nov. 29, 2018.

Joy of Android, "5 Best Real Digital Scale Apps for Android", Jan. 17, 2019.

Leo Simmons, "Estimating Body Mass Index from Face Images Using Keras and Transfer Learning", Feb. 11, 2019, https://medium.com/@leosimmons/estimating-body-mass-index-from-face-images-using-keras-and-transfer-learning-de25e1bc0212.

Pezzuolo et al., "Exploiting Low-cost depth Cameras for body Measurement in the Livestock Sector", Apr. 17, 2018, https://ercim-news.ercim.eu/en113/special/exploiting-low-cost-depth-cameras-for-body-measurement-in-the-livestock-sector.

Song et al., "Automated body weight prediction of dairy cows using 3-dimensional vision", J. Dairy Sci. 101:4448-4459, Apr. 29, 2017.

Stajnko et al., "Non Invasive Estimating of Cattle Live Weight Using Thermal Imaging", Jan. 16, 2015.

Thomas M. Banhazi et al., "Weight Estimation Using Image Analysis and Statistical Modelling: A Preliminary Study", Applied Engineering in Agriculture, 23(1):91-96, Jan. 2007.

Velardo et al., "Weight estimation from visual body appearance", Proc. of IEEE BTAS, 2010, https://www.researchgate.net/publication/224194520_Weight_estimation_from_visual_body_appearance.

Victoria Woollaston et al., "Turn your iPhone into Weighing Scales: Gravity app uses 3D Touch features to measure small items", 22:33 BST, Oct. 28, 2015.

* cited by examiner

SYSTEMS AND METHODS FOR WEIGHT MEASUREMENT FROM USER PHOTOS USING DEEP LEARNING NETWORKS

REFERENCE TO RELATED APPLICATIONS

This application is a non-provisional of and claims priority from U.S. Ser. No. 62/828,373, filed on 2 Apr. 2019, and entitled "SYSTEMS AND METHODS FOR WEIGHT ESTIMATION FROM USER PHOTOS USING DEEP LEARNING NETWORKS."

This application is also related to U.S. Ser. No. 16/741,620, filed on 13 Jan. 2020, and entitled "METHODS AND SYSTEMS FOR HEIGHT ESTIMATION FROM A 2D IMAGE USING AUGMENTED REALITY."

This application is also related to U.S. Ser. No. 16/195,802, filed on 19 Nov. 2018, which issued as U.S. Pat. No. 10,321,728, issued on 18 Jun. 2019, entitled "SYSTEMS AND METHODS FOR FULL BODY MEASUREMENTS EXTRACTION," which itself claims priority from U.S. Ser. No. 62/660,377, filed on 20 Apr. 2018, and entitled "SYSTEMS AND METHODS FOR FULL BODY MEASUREMENTS EXTRACTION USING A 2D PHONE CAMERA."

The entire disclosures of all referenced applications are hereby incorporated by reference in their entireties herein.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the U.S. Patent and Trademark Office files or records, but otherwise reserves all copyright and trade dress rights whatsoever.

FIELD OF THE INVENTION

Embodiments of the present invention are in the field of automated body measurements and pertain particularly to estimating body weights of users using photos taken with a mobile device.

BACKGROUND OF THE INVENTION

The statements in the background of the invention are provided to assist with understanding the invention and its applications and uses, and may not constitute prior art.

Obtaining an accurate estimate of a weight of a user has many useful applications. For example, fitness tracking and weight loss tracking require estimation of body weight. Similarly, accurately estimating clothing size and fit, which is based on body length measurements, can be performed with deep learning, but an accurate estimate of body weight is a valuable input for more accurate estimation of body length measurements.

Current methods of body weight measurement depend on utilizing weight scales, which are hardware components that are not always available. For example, not everyone has a scale in their home, and not everyone feels comfortable weighing themselves in a public gymnasium. With the advent of smart phones, users have come to expect seamless and instantaneous user experiences, using general purpose hardware, without utilizing specialized sensors or other hardware. Therefore, requiring users to purchase specialized weight scales for body weight measurements is not a feasible approach for many modern tech applications, and introduces unwanted user frictions. Similarly, in cases where accurate estimates of body weight are required for other tech applications, having users "guestimate" their own weight is hardly satisfactory.

Therefore, it would be an advancement in the state of the art to provide a system and method for accurately estimating a body weight from photos of a user taken using an ordinary 2D smartphone camera, such that everyone can easily take photos of themselves and benefit from accurate body weight estimation.

It is against this background that the present invention was developed.

BRIEF SUMMARY OF THE INVENTION

The present invention relates to methods and systems for extracting body weight estimates from user images, taken for example using a 2D mobile device camera.

More specifically, in various embodiments, the present invention is a computer-implemented method for estimating or predicting a body weight of a subject, the computer-implemented method executable by a hardware processor, the method comprising receiving one or more subject parameters; receiving one or more images containing the subject; identifying one or more annotation key points for one or more body parts underneath a clothing of the subject from the one or more images utilizing one or more annotation deep-learning modules; calculating one or more geometric features of the subject based on the one or more annotation key points; and generating a prediction of the body weight of the subject utilizing a weight machine-learning module based on the one or more geometric features of the subject and the one or more subject parameters.

In one embodiment, the one or more geometric features are selected from the group consisting of body part circumference(s), body part length(s), body image area(s), body part image area(s), body volume(s), and body part volume(s). In one embodiment, the body part circumference(s) comprise multiple body part circumferences for at least one body part.

In one embodiment, the generating the prediction of the body weight of the subject further comprises generating a feature vector comprising the one or more geometric features and the one or more subject parameters as input to the weight machine-learning module.

In one embodiment, the weight machine-learning module comprises one or more of a linear regressor, a nonlinear regressor, and a random forest algorithm, wherein the weight machine-learning module is trained on ground truth data comprising one or more sample body weights and one or more sample feature vectors for one or more sample subjects.

In one embodiment, the one or more of the subject parameters are used as normalization data to scale from pixel coordinates to real-world coordinates in the one or more images.

In one embodiment, a height of the subject is used as the normalization data. In one embodiment, a refence object of known size in the images is used as the normalization data.

In one embodiment, the one or more images comprises at least two images, wherein the at least two images contain the subject in at least two perspective views.

In one embodiment, the at least two images comprise at least a front-view image and a side-view image of the subject, wherein the generating the one or more geometric features based on the one or more annotation key points comprises one step selected from the group consisting of (a) calculating at least one circumference of at least one annotated body part utilizing annotated front-view and side-view images and a height of the subject, (b) calculating at least one body part image area of at least one annotated body part utilizing annotated front-view and side-view images and a height of the subject, and (c) calculating at least one body part volume of at least one annotated body part utilizing annotated front-view and side-view images and a height of the subject.

In one embodiment, the method further comprises after the receiving the one or more images performing body segmentation on the images to identify the one or more body parts associated with the subject from a background, wherein the body segmentation utilizes a segmentation deep-learning module that has been trained on segmentation training data, and wherein the segmentation training data comprise one or more images for one or more sample subjects and a body part segmentation for each body part for the one or more sample subjects.

In one embodiment, the annotation deep-learning modules utilize training data comprising one or more images for one or more sample subjects and one or more annotation key points for each body part for the one or more sample subjects.

In one embodiment, the one or more subject parameters are selected from the group consisting of a height, a received subject weight estimate, a gender, an age, an ethnicity, and a demographic information associated with the subject.

In one embodiment, the prediction of the body weight of the subject is a first estimate, wherein the method further comprises generating a second estimate of the body weight of the subject using a second machine-learning module, comparing a first confidence score of the first estimate and a second confidence score of the second estimate, and selecting either the first estimate or the second estimate as the body weight of the subject based on the first and the second confidence scores.

In one embodiment, the method further comprises determining whether the prediction of the body weight of the subject corresponds to a confidence level below a predetermined value, and in response to determining that the prediction of the body weight of the subject corresponds to a confidence level below the predetermined value, comparing the prediction of the body weight of the subject to a received subject weight estimate, updating the prediction of the body weight of the subject, wherein the received subject weight estimate is used to guide the weight machine-learning module, and replacing the prediction of the body weight of the subject with an updated prediction of the body weight of the subject.

In one embodiment, the subject parameters are received from a mobile computing device, and the subject images are received from a camera on the mobile computing device. In one embodiment, the receiving one or more subject parameters from the mobile computing device comprises receiving a measurement performed by the mobile computing device. In one embodiment, a depth data from a depth sensor on the mobile computing device is used as normalization data to scale from pixel coordinates to real-world coordinates in the one or more images.

In one embodiment, the method further comprises pre-processing the one or more images of the subject and a background before identifying the annotation key points, wherein the pre-processing comprises at least a perspective correction on the one or more images, and wherein the perspective correction is selected from the group consisting of perspective correction utilizing a head of the subject, perspective correction utilizing a gyroscope of the mobile computing device, and a perspective correction utilizing another sensor of the mobile computing device.

In various embodiments, a computer program product is disclosed. The computer program may be used for predicting body weight measurements of a subject, and may include a computer readable storage medium having program instructions, or program code, embodied therewith, the program instructions executable by a processor to cause the processor to perform the steps recited herein.

In various embodiment, a system is described for predicting body weight measurements, including a memory that stores computer-executable components; a hardware processor, operably coupled to the memory, and that executes the computer-executable components stored in the memory, wherein the computer-executable components may include a components communicatively coupled with the processor that execute the aforementioned steps.

In another embodiment, the present invention is a non-transitory, computer-readable storage medium storing executable instructions, which when executed by a processor, causes the processor to perform a process for predicting body weight measurements, the instructions causing the processor to perform the aforementioned steps.

In another embodiment, the present invention is a system for body weight measurement prediction using a 2D phone camera, the system comprising a device having a 2D camera, a processor, a display, a first memory; a server comprising a second memory and a data repository; a telecommunications-link between said device and said server; and a plurality of computer codes embodied on said first and second memory of said user-device and said server, said plurality of computer codes which when executed causes said server and said user-device to execute a process comprising the aforementioned steps.

In yet another embodiment, the present invention is a computerized server for predicting body weight measurements comprising at least one processor, memory, and a plurality of computer codes embodied on said memory, said plurality of computer codes which when executed causes said processor to execute a process comprising the aforementioned steps.

Other aspects and embodiments of the present invention include the methods, processes, and algorithms comprising the steps described herein, and also include the processes and modes of operation of the systems and servers described herein.

Yet other aspects and embodiments of the present invention will become apparent from the detailed description of the invention when read in conjunction with the attached drawings.

BRIEF DESCRIPTION OF THE DRAWINGS

Embodiments of the present invention described herein are exemplary, and not restrictive. Embodiments will now be described, by way of examples, with reference to the accompanying drawings, in which.

DETAILED DESCRIPTION OF THE INVENTION

With reference to the figures provided, embodiments of the present invention are now described in detail.

In the following description, for purposes of explanation, numerous specific details are set forth in order to provide a thorough understanding of the invention. It will be apparent, however, to one skilled in the art that the invention can be practiced without these specific details. In other instances, structures, devices, activities, and methods are shown using schematics, use cases, and/or flow diagrams in order to avoid obscuring the invention. Although the following description contains many specifics for the purposes of illustration, anyone skilled in the art will appreciate that many variations and/or alterations to suggested details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

In one embodiment, the system may automatically calculate (e.g., using one or more AI-based algorithms) body weight predictions using input photos of a subject, normalization data, and one or more subject parameters. Embodiments of the present invention do not require specialized hardware cameras, specialized weight scales, nor do they involve any special hardware whatsoever. Instead, advanced computer vision techniques utilizing deep-learning approaches combined with machine learning algorithms are used to predict accurate body weights no matter what the subject is wearing from photos provided from a simple mobile device camera. In the present disclosure, the term "2D phone camera" is used to represent any traditional camera embedded in, or connected to, computing devices, such as smart phones, tablets, laptops, desktops, and the like.

Deep Learning Networks and Machine Learning for Body Weight Prediction

Figure 1:
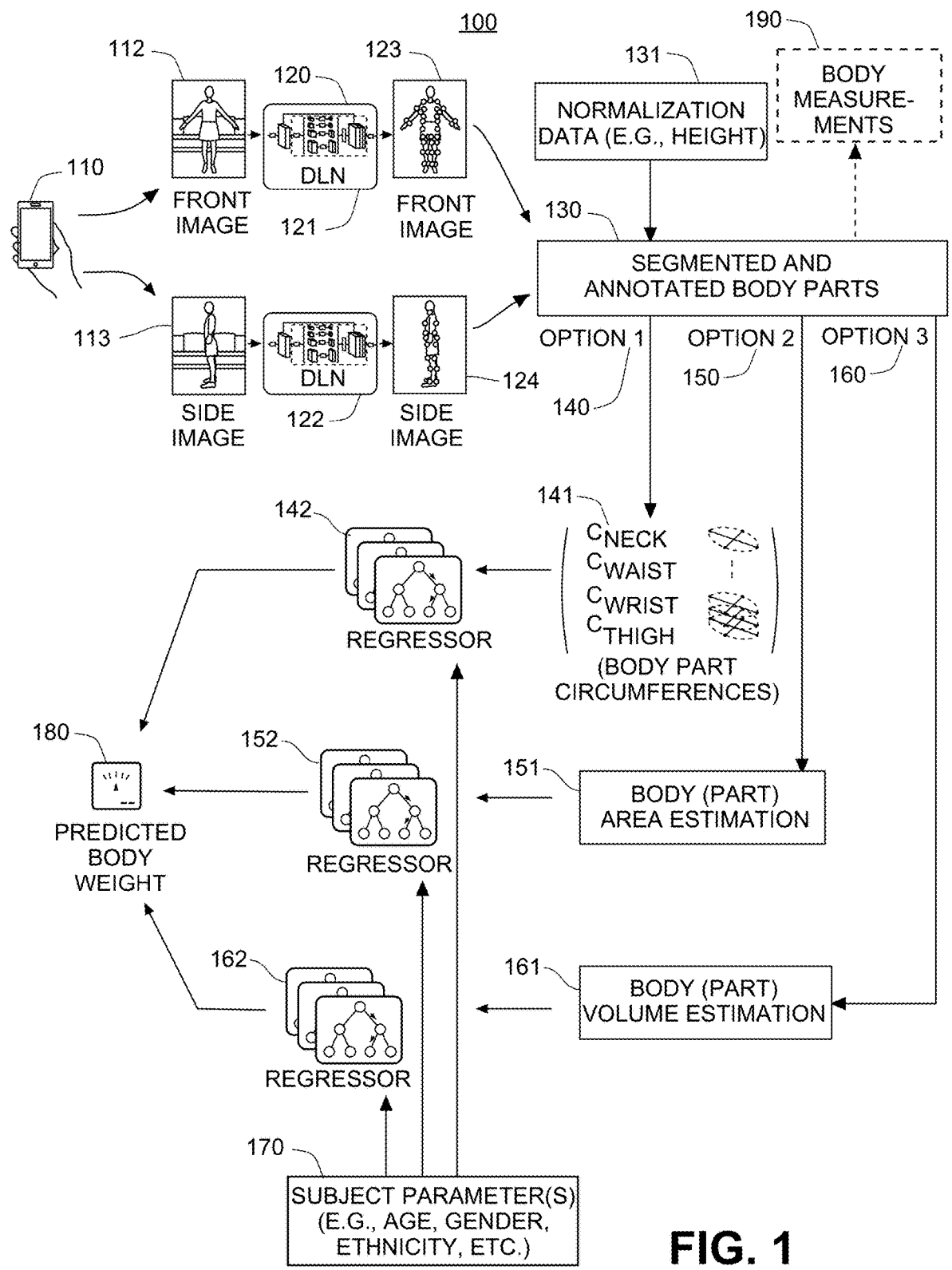
FIG. 1 shows an illustrative diagram for a body weight determination process utilizing deep learning networks (DLNs) and machine learning, in accordance with one embodiment of the invention.

FIG. 1 shows an illustrative diagram 100 for a body weight prediction process utilizing deep learning networks (DLNs) and machine learning, in accordance with one embodiment of the invention. At step 110, a mobile device with an ordinary 2D camera is utilized to obtain one or more images (e.g., front 112 and side 113 view images) of a human subject, as well as to receive one or more subject parameters. Subject parameters may include normalization data (e.g., a height of the human) or other subject parameters and are discussed in subsequent steps 131 and 170. At steps 120, one or more body parts (features) associated with the human are identified from the background, and one or more deep learning networks (121, 122) are utilized to annotate the one or more body parts (features) under the clothing the subject might be wearing in the images 112 and 113. In one embodiment, the identification of the human from the background is performed utilizing one or more segmentation deep-learning networks that have been trained on identifying the human body features (e.g., body parts) from the background. Also, in one embodiment, the annotation key points are generated for each body part utilizing one or more annotation deep-learning networks that have been trained on each body feature. This is shown in the annotated front-view 123 and side-view 124 images in FIG. 1. In one embodiment, annotation lines are also generated connecting body part key points, leading to line-annotated front- and side-view images. In step 130, the segmented and annotated body parts are combined with received normalization data (e.g., subject height) 131 in order to calculate an estimate of one or more geometric features (e.g., body part areas), where normalization data enables the conversion of measurements (e.g., distances between key annotation points) from pixel coordinates to real world coordinates. The generation and use of segmented and annotated body parts 130 with normalization data such as subject height 131 to estimate body measurements 190 is described in U.S. Pat. No. 10,321,728, which is hereby incorporated by reference herein.

FIG. 1 shows three possible embodiment options in steps 140, 150, and 160. In the first option 140, the geometric features are body part circumferences. According to this option, circumferences for one or more body parts 141 are generated from the annotated body parts (features). In one embodiment, the circumferences for the one or more body parts are generated using at least the front 123 and side 124 annotated images. In some embodiments, the circumferences for the one or more body parts are composed into a single body part circumference feature vector 141. At step 142, the body weight of the human subject is estimated or predicted utilizing a weight machine-learning module from the one or more body part circumferences 141 and the one or more subject parameters 170 (e.g., the height, age, gender, and/or ethnicity of the subject). In some embodiments, the inputs of the weight machine-learning module, comprising the one or more body part circumferences 141 and the one or more subject parameters 170, are aggregated into a single feature vector (not shown in FIG. 1). The weight machine-learning module 142, in some embodiments, may comprise one or more random forest regressors. Other machine learning methods are also within the scope of the weight machine-learning module, as described in greater detail below. Finally, at step 180, the predicted body weight (e.g., weight estimate) of the subject is output. The predicted body weight may be output to the user on the mobile computing device, or used for other downstream purposes by the mobile computing device or by another server process.

According to a second option 150, the geometric features are body part image areas, wherein areas for one or more body parts are generated from the annotated body parts (features) 151. In one embodiment, the areas for the one or more body parts are generated using at least front 123 and side 124 annotation key points. In some embodiments, the image areas for the one or more body parts are composed into a single body part area feature vector (not shown in FIG. 1). In some embodiments, the body area feature vector comprises the whole body areas from different body poses (e.g., a front whole body area and a side whole body area based on the annotated front-123 and side-124 images). In another embodiment, the body area feature vector comprises one or more body part areas based on one or more annotated images (e.g., one or more body part image areas based on annotated front-123 and side-124 images). At step 152, the body weight of the human subject is estimated utilizing a weight machine-learning module from the one or more body part areas 151 and the one or more subject parameters 170 (e.g., the height, age, gender, and/or ethnicity of the subject). In some embodiments, the inputs of the weight machine-learning module, comprising the one or more body part areas 151 and the one or more subject parameters 170, are aggregated into a single feature vector (not shown in FIG. 1). The weight machine-learning module 152 may comprise one or more random forest regressors. Finally, at step 180, the predicted body weight of the subject is output.

According to a third option 160, the geometric features are body part volumes, wherein volumes for one or more body parts are generated from the annotated body parts 161. In one embodiment, the volumes for the one or more body parts are generated using at least front 123 and side 124 annotation key points. In some embodiments, the volumes for the one or more body parts are composed into a single body volume feature vector (not shown in FIG. 1). In some embodiments, the body volume feature vector comprises an estimate of the whole body volume based on different body poses (e.g., the annotated front-123 and side-124 images). In another embodiment, the body volume feature vector comprises one or more body part volumes based on the one or more annotated images (e.g., the annotated front-123 and side-124 images). At step 162, the body weight of the subject is estimated utilizing a weight machine-learning module from the one or more body part volumes 161 and the one or more subject parameters 170 (e.g., the height, age, gender, and/or ethnicity of the user subject). In some embodiments, the inputs of the weight machine-learning module, comprising the one or more body part volumes 161 and the one or more subject parameters 170, are aggregated into a single feature vector (not shown in FIG. 1). The weight machine-learning module 162 may comprise one or more random forest regressors. Finally, at step 180, the predicted body weight of the subject is output.

Geometric Feature Calculation from Annotated Subject Images

In some embodiments of the first option 140, the annotation key points or annotation lines (e.g., annotated front-view 123 and side-view 124 body parts) are used to calculate a circumference for each body part (body feature) in real-world coordinates, such as centimeters (cm), inches (in), and so forth. For example, the distances between the front-view and side-view annotation key points of a neck feature can be used to calculate a neck circumference in centimeters. The calculated circumferences are utilized to generate the circumference feature vector 141. In one embodiment, hip and neck circumferences are used for the circumference feature vector. In another embodiment, leg and arm circumferences are used in any combination with the hip and/or neck circumferences to generate the circumference feature vector. In yet another embodiment, other body part circumferences are used in various sub-combinations to generate the circumference feature vector, as would be recognized by one of ordinary skill in the art. In some embodiments, the body part circumferences may comprise multiple body part circumferences for at least one body part. For example, more than two or more circumferences taken along the length of the body part (arm, thigh, and leg, etc.) may be utilized. In yet other embodiments, body part length(s), such as arm, leg, or torso lengths, may be utilized along with the body part circumference(s) to generate the subject feature vector.

Similarly, in some embodiments of the second option 150, the annotation key points (e.g., annotated front-view 123 and side-view 124 body parts) are used to calculate an image area for each body part (body feature) in real-world coordinates, such as square centimeters ($cm^2$), square inches ($in^2$), and so forth. For example, the distances between the front-view annotation key points 123 of various body parts (e.g., neck, waist, wrists, thighs, feet, etc.) can be used to calculate a front-view body image area in $cm^2$. In another embodiment, the front-view annotation key points 123 of various body parts (e.g., neck, waist, wrists, thighs, feet, etc.) can be used to calculate image areas for each body part in $cm^2$. The calculated image areas are utilized to generate the image area feature vector 151. In one embodiment, the front-view and side-view whole body image areas are used for the image area feature vector. In another embodiment, the front-view torso, leg, and arm body part image areas are used in any combination with the front-view and/or side-view whole body image areas to generate the image area feature vector. In yet another embodiment, other body part image areas are used in various sub-combinations to generate the image area feature vector, as would be recognized by one of ordinary skill in the art.

Furthermore, in some embodiments of the third option 160, the annotation key points (e.g., annotated front-view 123 and side-view 124 body parts) are used to calculate or estimate a volume for each body part (body feature) in real-world coordinates, such as cubic centimeters ($cm^3$), cubic inches ($in^3$), and so forth. For example, the distances between the front-view 123 and the side-view 124 annotation key points of various body parts (e.g., neck, waist, wrists, thighs, feet, etc.) can be used to calculate a body volume in $cm^3$. In another embodiment, the front-view 123 and side-view 124 annotation key points of various body parts (e.g., neck, waist, wrists, thighs, feet, etc.) can be used to calculate volumes for each body part in $cm^3$. The calculated volumes are utilized to generate the body volume feature vector 161. In one embodiment, the whole body volume is used for the volume feature vector. In another embodiment, the torso, leg, and arm body part volumes are used in any combination with the whole body volume to generate the volume feature vector. In yet another embodiment, other body part volumes are used in various sub-combinations to generate the volume feature vector, as would be recognized by one of ordinary skill in the art.

Figure 2:
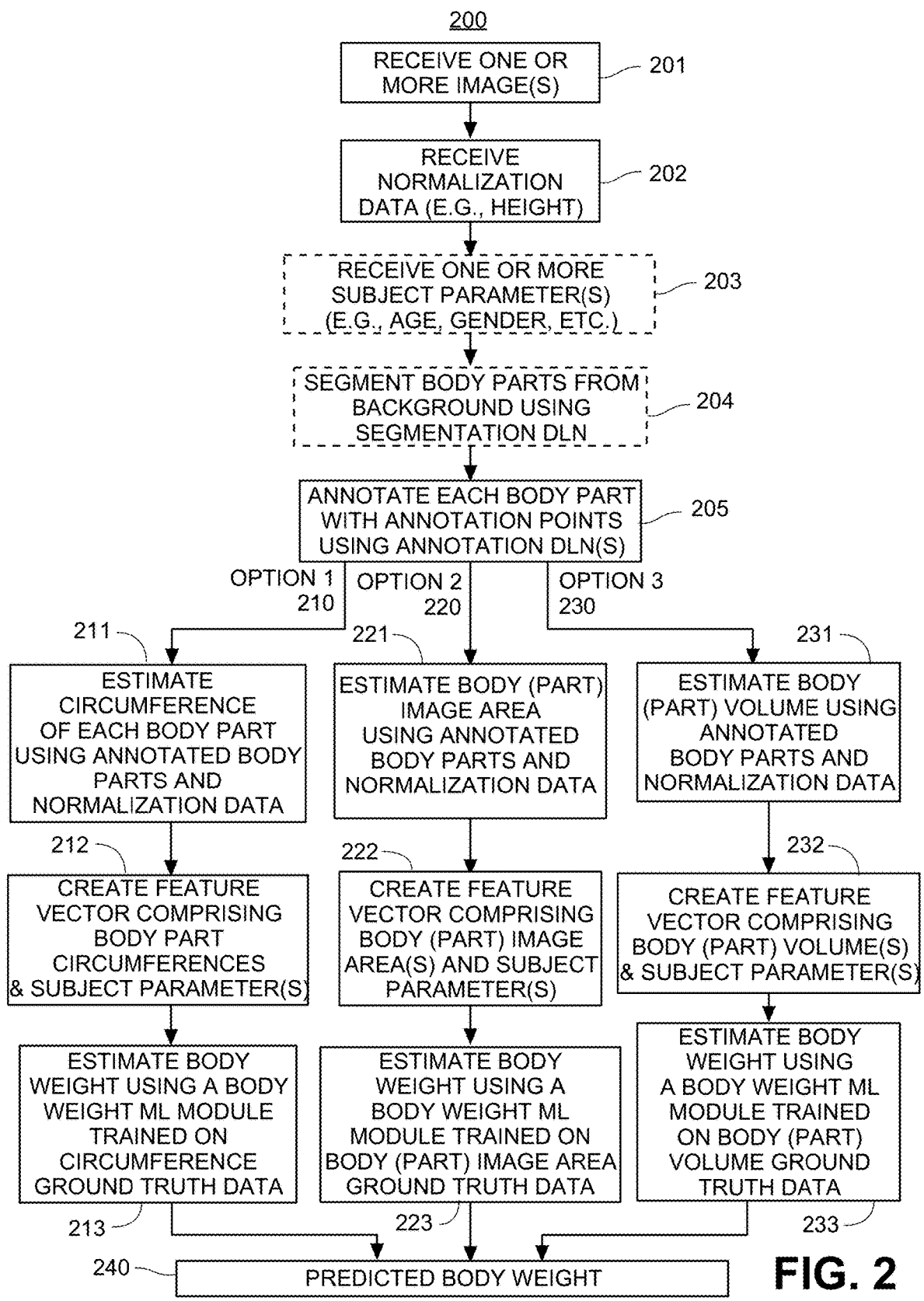
FIG. 2 shows an example flow diagram for a body weight determination process using deep learning networks (DLNs) and machine learning, in accordance with another embodiment of the invention.

FIG. 2 shows an example flow diagram 200 for a process for body weight prediction using deep learning networks (DLNs) and machine learning, in accordance with another embodiment of the invention. At step 201, the process comprises receiving one or more images from a computing device, the images containing the human subject and a background. At step 202, the process comprises receiving normalization data (e.g., subject height). As discussed previously, normalization data may also include a reference object of known size in the image, depth data from a depth sensor, and so on. Optionally, at step 203, the process comprises receiving one or more subject parameters (e.g., age, gender, ethnicity, etc.) from the computing device. Optionally, at step 204, the process comprises identifying one or more body features (e.g., body parts) associated with the human, for example by utilizing a segmentation deep-learning network that is utilized to segment body parts from the background. In FIG. 2, optional steps 203 and 204 are denoted by dashed boxes. At step 205, the process comprises annotating the one or more body features with annotation points corresponding to key body feature locations utilizing one or more annotation deep-learning networks that have been trained on each body feature. In the absence of optional step 204, step 205 automatically performs the identification of one or more body features (e.g., body parts) as part of the annotation step without first separating the body parts from the background. The annotated body parts from step 205 are then combined with received normalization data from step 202 in order to calculate or estimate one or more geometric features (e.g., body part circumferences, areas, or volumes). FIG. 2 shows three possible embodiment options in options 210 (body part circumferences), 220 (body part areas), and 230 (body part volumes). These options are similar to the options 140, 150, and 160 shown in FIG. 1.

In the first option 210, the geometric features are body part circumferences. According to this option, at step 211, the process comprises generating or estimating one or more body part circumferences from the annotated body parts and the normalization data (to convert from pixel to real-world coordinates). In some embodiments, step 211 comprises estimating the body parts circumferences using the annotated body parts and the height of the subject. In some embodiments, the body part circumferences are composed into one circumference feature vector 141. In step 212, the inputs of the weight machine-learning module, comprising the one or more body part circumferences and the one or more subject parameters, are aggregated into a single subject feature vector. In yet other embodiments, body part length(s), such as arm, leg, or torso lengths, may be utilized along with the body part circumference(s) to generate the subject feature vector. At step 213, the process comprises estimating or predicting the body weight of the subject utilizing a weight machine-learning module based on the subject feature vector, that has been trained on body part circumference/length ground truth data (e.g., data showing correlation between body part circumferences/lengths and body weights for given subject parameters, such as age, gender, ethnicity, and so on). Finally, at step 240, the process outputs the predicted body weight of the subject for downstream use.

In the second option 220, the one or more geometric features are body image areas or body part image areas. According to this option, at step 221, the process comprises generating or estimating one or more body part image areas from the annotated body parts and the normalization data. In some embodiments, step 221 comprises estimating the whole body image area, or one or more body parts image areas, using the annotated body parts and the height of the human. In some embodiments, the body part image areas are composed into a single body image area vector, as discussed above in the context of FIG. 1. In step 222, the inputs of the weight machine-learning module, comprising the one or more body part image areas and the one or more subject parameters, are aggregated into a single subject feature vector. At step 223, the process comprises estimating the body weight of the subject utilizing a weight machine-learning module based on the subject feature vector, that has been trained on body area ground truth data (e.g., data showing correlation between body (part) areas and body weights for given subject parameters, such as age, gender, ethnicity, and so on). Finally, at step 240, the process outputs the predicted body weight of the subject.

In the third option 230, the one or more geometric features are the body volume or one or more body part volumes. According to this option, at step 231, the process comprises generating or estimating one or more body part volumes from the annotated body parts and the normalization data. In some embodiments, step 231 comprises estimating a whole body volume, or one or more body part volumes, using the annotated body parts and the height of the human. In some embodiments, the body part volumes are composed into a single body volume feature vector, as discussed above in the context of FIG. 1. In step 232, the inputs of the weight machine-learning module, comprising the one or more body part volumes and the one or more subject parameters, are aggregated into a single subject feature vector. At step 233, the process comprises estimating the body weight of the subject utilizing a weight machine-learning module based on the subject feature vector, that has been trained on body volume ground truth data (e.g., data showing correlation between body (part) volumes and body weights for given subject parameters, such as age, gender, ethnicity, and so on). Finally, at step 240, the process outputs the predicted body weight of the subject.

It may be appreciated that the geometric features calculated from the annotation key points 350 are not limited to body part circumferences, body part image areas, and body part volumes, and may comprise any geometrical quantity measurable through the analysis of the received 2D images. For example, in one additional option (not shown in the FIGS. 1-3), the geometric features may include body part lengths measured in real-world coordinates from the annotation key points generated from the received photos at steps 313 and 323. These body part lengths may subsequently be included in the subject feature vector comprising the geometric features of the subject.

It may be appreciated that the geometric features may be used separately or in any combination. For example, both body part circumferences and body part lengths may be used together to generate the subject feature vector. In another example, body part circumferences, body part lengths, and body part image areas may all be used together to generate the subject feature vector. In yet another example, the body part volumes may be used separately or in combination with any or all of the other geometric features.

Subject Images/Photos

At step 201, one or more subject images or photos may be received from a user device, such as a mobile computing device, laptop, tablet, standalone camera, and so on. For example, at least front and/or side view photo(s) of a subject may be received. In one embodiment, the photos may be obtained from the device (e.g., mobile phone, laptop, tablet, etc.). In another embodiment, the photos may be obtained from a database (e.g., a social media database). In another embodiment, the subject photos include a photo showing a front view, and a photo showing a side view of the entire body of the subject. In some embodiments, only one photo, such as a front view, is utilized and the one photo is sufficient to perform accurate body weight prediction. In yet other embodiments, three or more photos are utilized, including in some embodiments, a front view photo, a side view photo, and a photo taken at an approximately 45-degree angle. Other combinations of subject photos are within the scope of the present invention, as would be recognized by one of ordinary skill in the art. In some embodiments, a subject video, for example, comprising a front view, a 90-, 180-, or even 360-degree view of the subject, may be received. From the subject video, one or more still frames or photos, such as a front view, a side view, and/or a 45-degree view of the subject are extracted from the video and used in the process that follows.

In one embodiment, the images may be taken at a specified distance (e.g., approximately 10 feet away from the camera of a computing device). In another embodiment, multiple images of a given position (e.g., front and side view photos) may be taken and an average image may be determined for each position. This may be performed to increase accuracy. In another embodiment, the subject may be positioned against a background of a specific type (e.g., a neutral color, or having a predetermined background image). In some embodiments, the subject may be positioned against any type of background. In one embodiment, the front and side view photos may be taken under similar lighting conditions (e.g., a given brightness, shadow, and the like).

In one embodiment, the images may be taken with the subject having a specific pose (e.g., arms in a predetermined position, legs spread at a shoulder length, back straight, etc.). In one embodiment, the input images show the subject posing with hands at 45 degrees ("A-pose"). Although a specific user pose such as the "A-pose" may be used in some embodiments, it will be understood to one of ordinary art that any pose, including the "A-pose," hands on the side, or any other pose, is within the scope of the present invention. An optimal pose would clearly show legs and arms separated from the body. One advantage of the present invention is that a subject can stand in almost any reasonable pose, against any type of background. The subject does not need to stand against a blank background or make special arrangements for where the photos are taken.

In one embodiment, the subject may indicate whether the subject is dressed in tight, normal, or loose clothing for more accurate results. In one embodiment, the front and side view photos may include images of the subject wearing normally fitted clothing (e.g., not extra loose or extra tight). Alternatively, or additionally, the front and side view photos may include images of the subject partially clothed (e.g., shirtless), or having a different type of fit (e.g., tight, loose, etc.) depending on the embodiment.

Figure 3:
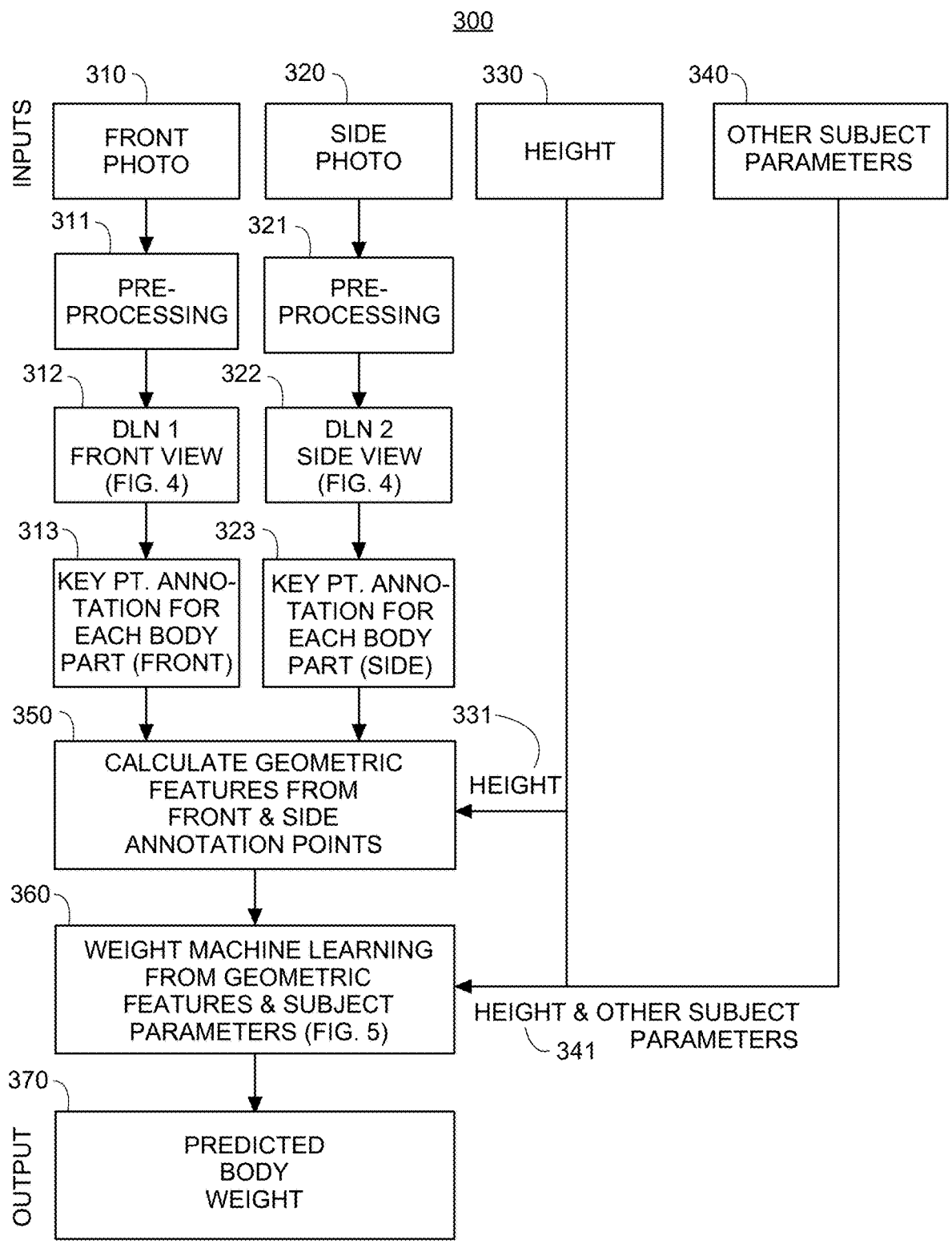
FIG. 3 shows a detailed flow diagram for body weight determination using deep learning networks (DLNs) and machine learning, in accordance with another embodiment of the invention.

FIG. 3 shows a detailed flow diagram 300 for body weight prediction using deep learning networks (DLNs) and machine learning, in accordance with another embodiment of the invention. Inputs to the body weight prediction process include a front photo 310, a side photo 320, a subject height 330, and other subject parameters (e.g., subject weight estimate, age, gender, ethnicity, etc.) 340. The front photo 310 is pre-processed in step 311, while the side photo 320 is pre-processed in step 321. Examples of pre-processing steps, such as perspective correction, human cropping, image resizing, are discussed below. At step 312, the pre-processed front photo is used as input to DLN 1 (described in more detail in relation to FIG. 4) to extract annotation key points for the front photo 310. At step 322, the pre-processed side photo is used as input to DLN 2 to analogously extract annotation key points for the side photo 320. The annotation key points for each body part from the front view 313 are output from DLN 1 and the annotation key points for each body part from the side view 323 are output from DLN 2. At step 350, the two sets of annotation key points from the front photo 310 and the side photo 320 are utilized along with the normalization data (e.g., height) 331 to calculate the geometric features discussed in relation to FIGS. 1 and 2 (e.g., body part circumferences, areas, and/or volumes). At step 360, the geometric features, along with the height and other subject parameters 341 are utilized in a machine learning algorithm, such as a random forest (described in more detail in relation to FIG. 5), to predict one or more subject body weight estimates. Finally, at step 370, the predicted body weight is output.

Subject Parameters

In some embodiment, one or more of the subject parameters are utilized as input to the weight machine-learning module. For example, height, age, gender, ethnicity, athleticism, and other subject parameters may be used as input to the weight machine-learning module, as would be recognized by one of ordinary skill. In particular, and in accordance with one embodiment, the subject's own best "guestimate" of their own weight may also be used as a subject parameter as input to the weight machine-learning module. As one illustrative example, the gender of the subject may be used as one subject parameter as input to the weight machine-learning module. For example, women may have more fat distribution in the body, and may therefore have a different density from men, and hence the gender of the human subject may be one useful parameter for input to the weight machine-learning module. There are many other subject parameters that would be similarly within the scope of the present invention as input to the weight machine-learning module, as would be recognized by one of ordinary skill in the art. The weight machine learning module may discover previously unrecognized user parameters as being important in the correlation between the user parameters and the body weight.

Subject parameters (e.g., height, weight, demographics, athleticism, and the like) may be received from a user and/or the parameters may be auto-generated by a camera on the mobile computing device. In various aspects, the subject parameters may be determined automatically (e.g., using computer vision algorithms or mined from one or more databases), or received from the user (e.g., user input).

In various embodiments, steps 201 (receive input images), 202 (receive normalization data), and 203 (receive subject parameters) may be performed in any order in various embodiments of the present invention, or the steps may be implemented in parallel. In some embodiments, the normalization data is one of the subject parameters (e.g., subject height), so steps 202 and 203 are effectively combined.

In another embodiment, a received subject weight estimate may be received and used in conjunction with the height. Both subject parameters may be determined or estimated automatically (e.g., using computer vision algorithms or mined from one or more databases), or received from the user (e.g., user input). In one embodiment, from these subject parameters, a body mass index (BMI) may be calculated. The BMI may be used to improve accuracy of the body weight prediction using both the received subject weight estimate and the height.

Thus, subject parameters may include one or more of height, received subject weight estimate, gender, age, ethnicity, country of origin, athleticism, and/or other demographic information associated with the subject, among others. The subject parameters, such as the height, received subject weight, BMI index, age, gender, and so forth, are used to generate the feature vector for body weight prediction. In various embodiments, the subject parameters may be obtained automatically from the device, from one or more third-party data sources, or from the server.

Normalization Data and Subject Height

In various embodiments of the invention, the normalization data (131, 202) may comprise one of the subject parameters, such as the subject height 330. The normalization data is obtained, generated, and/or measured in order to perform a normalization or a scaling from pixel coordinates to real-world coordinates.

In one embodiment, the subject height is used to normalize, or scale, front and/or side-view photos and provide a reference scale for the subject in the photo. In one embodiment, the subject height is received from a measurement performed by the mobile computing device. In one embodiment, the subject height is known from a prior measurement, a prior user input, and/or from a database query. In one embodiment, the subject height is measured by the mobile computing device using a height measurement process using a position guide in augmented reality (AR) as described in related U.S. Ser. No. 16/741,620, filed on 13 Jan. 2020, and entitled "METHODS AND SYSTEMS FOR HEIGHT ESTIMATION FROM A 2D IMAGE USING AUGMENTED REALITY," which is incorporated by reference herein.

In one embodiment, the system may determine the geometric features using as input the subject height received to normalize the image data from pixel to real-world coordinates (e.g., centimeters). In order to do this, the annotation DLN in one embodiment draws a "full body" annotation line with two annotation points indicating a location of the subject's height, with a dot representing a bottom of the subject's feet and another dot representing a top of the subject's head. This "fully body" annotation line is used to normalize the distances between annotation key points by the subject's known height provided in steps 131, 202, or 330. In other words, the height of the subject in the image is detected and used along with the received actual height to normalize all annotation key point measurements. This process may be thought of as "height reference normalization," using the subject's known height as a standard measurement for normalization. Once the normalization is performed, real-world distances (circumferences and lengths), areas, and volumes of body parts may be calculated, predicted, or estimated from the pixel distances (circumferences and length) and pixel areas of body parts in the input images.

In yet another embodiment, the normalization data can be real-world coordinates mapped by a depth sensor onto the input images. Depth sensor data can therefore be used to convert the known position of the subject from pixel coordinates into real-world coordinates. The depth sensor provides Z-coordinate data, where the Z-axis is away from the camera, which can be used to normalize the distance to the subject from pixels to real-world coordinates. This is performed analogously to height reference normalization.

In yet another embodiment, the normalization data may be an object of a known size serving as scale reference, such as a letter or an A4 sheet of paper, a credit card, and so on. In preparation for capturing an image of the subject, a rectangular reference object, for example an 8.5×11 sheet of paper or a credit card, is placed on or in near proximity to the subject. The size and aspect ratio of the reference rectangle can be determined via different methods, explicitly or automatically determined. In one embodiment, the user can identify the reference rectangle used, such as an A4 or 8.5×11 paper, a 3×5 notecard, or an ISO/IEC standard dimension credit card. Then, a rectangle scoring algorithm can find the explicitly identified rectangle. That is, the normalization data to scale from pixel to real-world coordinates can receive dimensions of the reference rectangle from the user. In another embodiment, the process determines the size of the reference rectangle automatically based upon characteristics of the captured image when compared to a data store of common document sizes. Multiple rectangles in a picture can be found, one rectangle can be selected, and the rectangle's dimensions deduced from a list of allowed dimensions and aspect ratios. Alternatively, the size and rounded corners as well as any text or logo on the reference rectangle could indicate that it is a credit card, and the size deduced from known credit card sizes. In another embodiment, the user may be required to select from a supplied list of common items which could be used as a reference rectangle, such as a credit card, a dollar bill, or a sheet of standard sized paper.

Pre-Processing of Subject Images

In some embodiments, pre-processing on the one or more photos of the subject, such as a perspective correction, may be performed on the front 311 and side 312 view photos, if needed. For example, the system may use OpenCV, an open-source machine vision library, and may make use of features of the head in the front and side view photos and the subject's height as references for perspective correction. In this way, embodiments of the invention may more accurately determine body measurements, such as torso length and leg length, and annotation key points. Optionally, a perspective side photo showing where the camera is positioned relative to the person being photographed may yield even more accurate perspective correction by allowing the system to calculate the distance between the camera and the subject. In some embodiments, the system may instead use gyroscope data provided by the device (or a peripheral device connected to the device, such as an attached computer device) to detect a photo perspective angle, and perform perspective correction based on this photo perspective angle.

In some embodiments, one or more additional pre-processing steps (not shown in FIGS. 1-3) may be performed on the one or more photos of the user. Various computer vision techniques may be utilized to further pre-process the one or more images. Other examples of pre-processing steps may include contrast, lighting, and other image processing techniques to improve the quality of the one or more images before further processing.

Segmentation Deep Learning Network (DLN)

In some embodiments of the present invention, computer vision techniques and deep learning are applied to a front view and a side view photo of the subject, plus the subject's height, to detect key points of the subject's body under the clothing using one or more deep learning networks that have been trained on images from thousands of sample subjects along with the subject's body outlines under the clothing. The key point annotations are used together with the subject's height to generate one or more geometric feature measurements for the subject in real-world coordinates. The geometric feature measurements are used with the height and possibly other subject parameters (such as gender, age, ethnicity, etc.), to predict the subject's body weight using one or more machine learning modules that have been trained on the sample subjects' ground truth weight data. As more data is collected by the system, the accuracy of the predicted body weight automatically improves.

As described above, geometric feature measurements (that is the lengths, circumferences, areas, and/or volumes of one or more body parts), are used as input to the weight machine-learning module to predict the subject's body weight. In some embodiments, body feature segmentation from the background and body feature key point annotation for geometric feature measurement are performed using one or more deep-learning networks. Accordingly, the segmentation and annotation deep-learning networks used for key point annotation for detecting the subject's body under the clothing are now described in detail.

At steps 204 and 706, a body feature, such as a body part of the subject (e.g., a neck, an arm, a leg, etc.) may be segmented from the image using a first deep learning network (DLN), known as a segmentation DLN. In one embodiment, "deep learning" may refer to a class of machine learning algorithms that use a cascade of multiple layers of nonlinear processing units for feature extraction and transformation modeled after neural networks. In one embodiment, the successive layers may use the output from the previous layer as input. In one embodiment, the "deep" in "deep learning" may refer to the number of layers through which the data is transformed. An example of a body feature segmentation DLN is explained and shown in reference to FIG. 4 below.

Before performing this segmentation step on data from a real user, the system may have been trained first, for example, on sample photos of humans posing in different environments in different clothing against different background, for example, with hands at 45 degrees, sometimes known as the "A-pose." In one embodiment, the segmentation DLN algorithm may be trained with segmentation training data. In some embodiments, the segmentation training data may include thousands of sample photos with humans having segmented body features. The sample photos segment the body features from the background of the photos.

In some embodiments, the training data includes medical data, for example from CAT scans, MRI scans, and so forth. In some embodiments, the training data includes data from previous 3D body measurements that include 3D body scans from 3D body scanners. In some embodiments, the 3D body scans may be used to extract approximate front and/or side view photos, in cases where the front and side view photos are not explicitly available. In some embodiments, the ground truth data comprises data from 3D body scans. In some embodiments, 3D body scan data from the "SizeUSA" data set, which is a commercial sample of 3D body scans obtained on about 10,000 human subjects (both male and female), may be utilized. In other embodiments, 3D body scan data from the "CAESAR" data set may be utilized, which is another commercial sample of 3D body scans obtained on about 4,000 human subjects, and also includes ground truth data. In yet other embodiments, an organization utilizing the present invention may capture their own front and side photos, along with suitable ground truth data, for training the segmentation DLN.

In one embodiment of the present invention, the identified body parts may be segmented, separated, or cropped from the rest of the human and the background using a segmentation map generated in steps 204 and 706. The cropping may be actual or virtual cropping. The part of the image corresponding to each identified body part may be cropped, segmented, or separated from the rest of the image, and that part of the image passed to the annotation step (205 and 708). By cropping or separating the identified body parts from the rest of the image, the DLN used in the annotation step (205 and 708) can be specially or separately trained on each separate body part, increasing both accuracy and reliability.

Annotation Deep Learning Networks (DLNs)

At step 205, annotation key points or an annotation line for each body part that was identified at step 204 may be drawn to detect the subject's body shape under the clothing using one or more deep learning networks (DLNs), known as annotation DLNs. In one embodiment, there is one annotation DLN for the entire body. In another embodiment, there is a separate annotation DLN for each body part. An advantage of using a separate annotation DLN for each body part is increased accuracy and reliability in body part annotations. Each body part annotation DLN may be separately trained on separate and unique data for each body part. The specificity of data on each body part increases the accuracy and reliability of the DLN, and also increases the speed of convergence of the neural network layer training. An example of a body feature key point annotation DLN is explained and shown in reference to FIG. 4 below.

In one embodiment, the annotation DLN identifies annotation key points or annotation lines from signals obtained from the body features. Annotation key points and annotation lines may be different for each body feature and may be drawn differently. For example, for the bicep width or circumference, the system may draw a line perpendicular to the skeletal line at the bicep location; for the chest, the system may connect two chest dots instead. From the annotation of each body feature, a body feature measurement may then be obtained by normalizing on the subject's height received in steps 131, 202, or 330, as described further below.

Before performing this annotation step on data from a real subject, the system may have been trained first, for example, on sample photos of humans posing in different environments wearing different clothing, for example, with hands at 45 degrees, sometimes known as the "A-pose", as described further below. The sample photos identify the body features and key points annotations of the subjects under the clothing.

For the deep learning networks (DLNs) used in the present invention, any suitable deep learning architecture may be used, such as deep neural networks, deep belief networks, and/or recurrent neural networks. In some embodiments, the deep learning algorithms may learn in supervised (e.g., classification) and/or unsupervised (e.g., pattern analysis) manners. Further, the deep learning algorithms may learn multiple levels of representations that correspond to different levels of abstraction of the information encoded in the images (e.g., whole body, body part, etc.). In some embodiments, the images (e.g., the front and side photos) may be represented as a matrix of pixels. In one embodiment of the DLN, the first representational layer of the DLN may abstract the pixels and encode edges; the second layer may compose and encode arrangements of edges; the third layer may encode a nose and eyes; and the fourth layer may recognize that the image contains a face or other body feature, and so on.

Illustrative Deep Learning Network (DLN) Module Architecture

Figure 4:
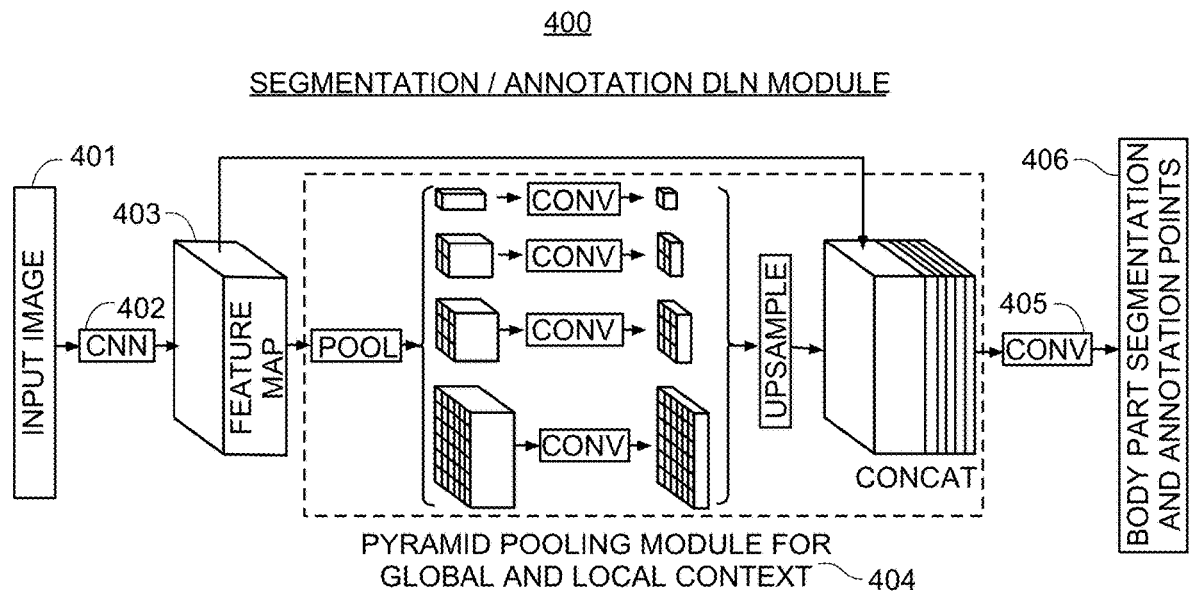
FIG. 4 shows a detailed flow diagram for body part segmentation and annotation using deep learning networks (DLNs), in accordance with one embodiment of the invention.

FIG. 4 shows a detailed flow diagram 400 for body part segmentation and annotation, in accordance with one embodiment of the invention. In one embodiment, the body part segmentation and annotation is done using a deep learning network (DLN) using training data as described above. In one embodiment, the body part segmentation and annotation is performed using a convolutional neural network (CNN) combined with a pyramid scene parsing network (PSPNet) for improved global and local context information. In a PSPNet, the process may utilize global & local context information from different sized regions that are aggregated through a "pyramid pooling module." As shown in FIG. 4, at least one input image 401 is first passed through a convolutional neural network (CNN) 402 to obtain a feature map 403 which classifies or segments each pixel into a given body part and/or annotation point. Next, global & local context information is extracted from the feature map utilizing the pyramid pooling module 404, which aggregates information from the image on different size scales. Finally, the data is passed through a final convolution layer 405 to classify each pixel into body part segments and/or annotation key points 406.

In greater detail, from an input image 401, a CNN 402 is first used to obtain a feature map 403, then a pyramid pooling module 404 is used to extract different sub-regions' features; followed by up-sampling and concatenation layers to form the final feature representation, which carries both local and global context information. Finally, the feature representation is fed to a final convolution layer 405 to obtain the final per-pixel prediction. In the example shown in FIG. 4, the pyramid pooling module 404 combines features under four different scales. The largest scale is global. The subsequent levels separate the feature map into different sub-regions. The output of different levels in the pyramid pooling module 404 comprise the feature map under different scales. In one embodiment, to maintain the weight of the global features, a convolution layer may be used after each pyramid level to reduce the dimension of context representation. Next, the low-dimension feature maps are up-sampled to get the same size features as the original feature map. Finally, the different feature levels are concatenated with the original feature map 403 for the pyramid pooling module 404 output. In one embodiment, by using a four-level pyramid, as shown, the pooling windows cover the whole, half, and smaller portions of the original image 401.

In one embodiment, the PSPNet algorithm is implementation as described in Hengshuang Zhao, et al., "Pyramid Scene Parsing Network," CVPR 2017, Dec. 4, 2016, available at arXiv:1612.01105, which is hereby incorporated by reference in its entirety as if fully set forth herein. PSPNet is only one illustrative deep learning network algorithm that is within the scope of the present invention, and the present invention is not limited to the use of PSPNet. Other deep learning algorithms are also within the scope of the present invention. For example, in one embodiment of the present invention, a convolutional neural network (CNN) is utilized to extract the body segments (segmentation), and a separate CNN is used to annotate each body segment (annotation).

Illustrative Machine Learning (ML) Module Architecture

Figure 5:
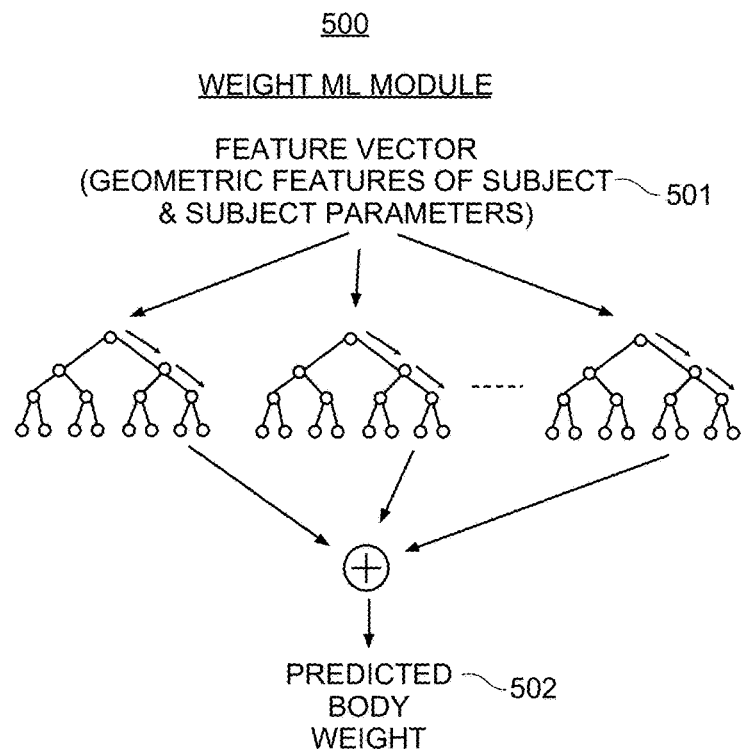
FIG. 5 shows an illustrative diagram for a machine learning algorithm for body weight determination from one or more feature vectors obtained from the geometric features calculated based on key point annotations and one or more subject parameters, in accordance with another embodiment of the invention.

FIG. 5 shows an illustrative diagram 500 for a machine learning (ML) module for body weight prediction 502 from one or more subject feature vectors 501 comprising geometric features obtained from the deep learning networks (DLNs), in accordance with one embodiment of the invention. FIG. 5 shows geometric features of the subject (e.g., body part circumferences, areas, and/or volumes) and subject parameters (e.g., height) as the input feature vector 501. That is, the input to the ML module is the subject feature vector 501, which may comprise, for example, the circumferences, areas, and/or volumes of the body parts obtained from the deep-learning networks, the height, and the other subject parameters, as described, for example, in option 1 (steps 140 and 210) of FIGS. 1-2. The output of the ML module is the predicted body weight 502.

In one embodiment, shown schematically in FIG. 5, the ML module uses a random forest algorithm, which is an illustrative machine learning algorithm. The random forest algorithm use a multitude of decision tree predictors, such that each decision tree depends on the values of a random subset of the training data, which minimizes the chances of overfitting. In one embodiment, the random forest algorithm is implementation as described in Leo Breiman, "Random Forests," Machine Learning, 45, 5-32, 2001, Kluwer Academic Publishers, Netherlands, Available at doi.org/10.1023/A:1010933404324, which is hereby incorporated by reference in its entirety as if fully set forth herein. The random forest algorithm is only one illustrative machine learning algorithm that is within the scope of the present invention, and the present invention is not limited to the use of random forest.

Once the geometric features are calculated (e.g., steps 141, 151, 161 in FIG. 1), a body weight prediction may be made using one or more weight machine learning (ML) algorithms. In one embodiment, the weight ML algorithm comprises a random forest machine learning module. In some embodiments, there is one weight ML module for the entire body. In one embodiment, there is a separate weight ML module for each body part, whereby the predicted body weight is the sum of the predicted body part weights. For example, in the third option of FIGS. 1 and 2 (steps 160 and 230), a separate ML module can predict the weight of a given body part based on a body part feature vector comprising the area or volume of that body part and the one or more subject parameters. Finally, the predicted body weight is the sum of the predicted weights of all the subject's body parts.

It may be appreciated that random forests are selected in the examples above as the weight ML module algorithm by way of illustration and not limitation, and that other ML algorithms can be implemented for the weight ML module such as, but not limited to, other linear and non-linear regressors, such as K-means clustering and Support Vector Machines (SVMs), in accordance with the examples disclosed herein. A simple linear regressor, such as a correlation coefficient, may also be utilized in some embodiments. The correlation coefficient may simply correlate the body weight with the body volume for a given gender, age, and so forth. Other machine learning algorithms, including but not limited to, nearest neighbor, decision trees, support vector machines (SVM), Adaboost, Bayesian networks, various neural networks including deep learning networks, evolutionary algorithms, and so forth, are also within the scope of the present invention for implementing the weight ML module.

In embodiments of the present invention, the weight ML module is trained on ground truth data comprising one or more sample body weights and one or more sample feature vectors for one or more sample subjects. For example, in the embodiments of the first option (steps 140 and 210 in FIGS. 1 and 2), the weight ML module is trained on ground truth data comprising one or more sample body weights and one or more sample feature vectors, wherein the sample feature vectors comprise one or more subject parameters and one or more body part circumferences. Similarly, in the embodiments of the second option (steps 150 and 220 in FIGS. 1 and 2), the weight ML module is trained on ground truth data comprising one or more sample body weights and one or more sample feature vectors, wherein the sample feature vectors comprise one or more subject parameters and one or more body part image areas. Moreover, in the embodiments of the third option (steps 160 and 230 in FIGS. 1 and 2), the weight ML module is trained on ground truth data comprising one or more sample body weights and one or more sample feature vectors, wherein the sample feature vectors comprise one or more subject parameters and one or more body part volumes.

It may be appreciated that the first option (steps 140 and 210 in FIGS. 1-2) yields the simplest ML module implementation, as circumference calculations involve simpler operations. However, the associated ML module is expected to be less accurate since body part circumference training data does not offer as much information as body part areas or volumes. On the other hand, the third option (steps 160 and 230 in FIGS. 1-2) may require subject photos and accompanying 3D body scans as training data, along with sample body weights and other subject parameters. This option requires more complex training data, requires more complex operations, such as converting key point annotations in the 2D images to 3D body part volume estimates, and but is likely to lead to the highest accuracy body weight predictions. The second option (steps 150 and 220 in FIGS. 1-2) may be regarded as a compromise option that is expected to require moderate processing complexity and to yield sufficiently accurate results.

As noted, embodiments of devices and systems (and their various components) described herein can employ artificial intelligence (AI) to facilitate automating one or more features described herein (e.g., providing body extraction, body segmentation, weight measurement extraction, and the like). The components can employ various AI-based schemes for carrying out various embodiments/examples disclosed herein. To provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system, environment, etc. from a set of observations as captured via events and/or data. Determinations can be employed to identify a specific context or action, or can generate a probability distribution over states, for example. The determinations can be probabilistic—that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, etc.)) schemes and/or systems (e.g., support vector machines, neural networks, expert systems, Bayesian belief networks, fuzzy logic, data fusion engines, etc.) in connection with performing automatic and/or determined action in connection with the claimed subject matter. Thus, classification schemes and/or systems can be used to automatically learn and perform a number of functions, actions, and/or determinations.

A classifier may map an input feature vector (e.g., subject feature vector) to a confidence level that the input belongs to a class, such as a weight band range (e.g., 68±1 kg). Such classification may employ a probabilistic and/or statistical-based analysis (e.g., factoring into the analysis utilities and costs) to determinate an action to be automatically performed. Various directed and undirected model classification approaches include, e.g., support vector machines (SVMs), naive Bayes, Bayesian networks, decision trees, neural networks, fuzzy logic models, and/or probabilistic classification models providing different patterns of independence can be employed. Classification as used herein also is inclusive of statistical regression that is utilized to develop models of priority. In short, various machine learning methods, algorithms, and modules are within the scope of the present invention.

Training the Deep Learning Networks (DLNs) and Machine Learning (ML) Modules

Training the segmentation DLN, the annotation DLN, and the weight ML which are utilized in generating body weight measurements is now described in accordance with example embodiments of the present invention. The training algorithm receives one or more photos. For example, front and side view photos of a given subject may be received. In another embodiment, the photos may be obtained from the device (e.g., mobile phone, laptop, tablet, etc.). In another embodiment, the photos may be obtained from a database (e.g., a social media database).

As noted, in one embodiment, the images may be taken at a specified distance (e.g., approximately 10 feet away from the camera of a computing device). In one embodiment, the images may be taken with the subject having a specific pose (e.g., arms in a predetermined position, legs spread at a shoulder length, back straight, "A-pose," etc.). In another embodiment, multiple images of a given position (e.g., front and side view photos) may be taken and an average image may be determined for each position. This may be performed to increase accuracy. In another embodiment, the subject may be positioned against a background of a specific type (e.g., a neutral color, or having a predetermined background image). In another embodiment, the front and side view photos may be taken under similar lighting conditions (e.g., a given brightness, shadow, and the like). In another embodiment, the front and side view photos may include images of the subject wearing normally fitted clothing (e.g., not extra loose or extra tight). Alternatively, and/or additionally, the front and side view photos may include images of the subject partially clothed (e.g., shirtless), or having a different type of fit (e.g., tight, loose, etc.) depending on the embodiment.

In some embodiments, one or more pre-processing steps such as a perspective correction may be performed on the front and side view photos, if needed. For example, the system may use OpenCV, an open source machine vision library, and may make use of features of the head in the front and side view photographs and the subject's height as references for perspective correction. In this way, embodiments of the disclosure may avoid determining weight measurements which are inaccurate. Optionally, a perspective side photo showing where the camera is positioned relative to the person being photographed may yield even more accurate perspective correction by allowing the system to calculate the distance between the camera and the subject. In some embodiments, the system may instead use gyroscope data provided by the device (or a peripheral device connected to the device, such as an attached computer device) to detect a photo perspective angle, and perform perspective correction based on this photo perspective angle. Other pre-processing steps, such as contrast, lighting, or other image processing techniques may be utilized to pre-process the received images in order to facilitate the following steps.

After receiving the photos, an annotator may segment body features, such as body parts, from the background. In one embodiment, the body parts may be color-coded for convenience. In particular, body segmentation may be performed by a human to extract a subject from a background of the photos. For example, the annotator may be used to visually edit (e.g., trace out and color code) photos and indicate which body parts correspond to which portions of the photos to extract the subject from the background. In one embodiment, the photos may include subjects posing in different environments in different clothing, with hands at 45 degrees ("A-pose"). As noted, accurate body outlines may be drawn by human annotators from the background. The body outlines may be drawn on any suitable software platform, and may use a peripheral device (e.g., a smart pen) for ease of annotation. Further, at least a portion of such segmented images may be used as training data that may be fed to the deep learning network, so a graphical processing unit (GPU) can learn from outlines of humans in the A-pose wearing any clothes in any background. In one embodiment, the segmented images are utilized to train the segmentation DLN used in step 204 of FIG. 2.

The annotator may then draw estimated annotation key points or lines for each body feature under the clothing. As noted, accurate annotation lines may be drawn by annotators estimating the body under the clothing. The annotation lines may be drawn on any suitable software platform, and may use a peripheral device (e.g., a smart pen) for ease of annotation. Further, at least a portion of such annotated images may be used as training data that may be fed to the deep learning network, so a GPU can learn from annotation points of humans in the A-pose wearing any clothes in any background. In one embodiment, the key point annotations are utilized to train the annotation DLN used in step 205 of FIG. 2.

Actual body weight measurements for each subject (e.g., as determined by a scale) may be received to serve as ground-truth data. The actual body weight measurements may be used as validation data and used for training the algorithms used by the system. For example, the actual body weight measurements may be used in minimizing an error function or loss function (mean squared error, likelihood loss, log-loss, hinge loss, etc.) associated with the machine learning algorithms. In one embodiment, the ground-truth body weight data is utilized to train the weight ML used in steps 213, 223, or 232 of FIG. 2.

In some embodiments, the training of the deep learning networks may be performed using training data that is generated as described in related applications U.S. Ser. No. 16/517,391, filed on 19 Jul. 2019, which issued as U.S. Pat. No. 10,489,683, issued on 26 Nov. 2019, entitled "METHODS AND SYSTEMS FOR AUTOMATIC GENERATION OF MASSIVE TRAINING DATA SETS FROM 3D MODELS FOR TRAINING DEEP LEARNING NETWORKS," which itself claims priority from U.S. Ser. No. 62/780,737, filed on 17 Dec. 2018, entitled "SYSTEMS AND METHODS FOR GENERATING MASSIVE TRAINING DATA SETS FOR TRAINING DEEP LEARNING NETWORKS FOR BODY MEASUREMENTS," the entire disclosures of which are hereby incorporated by reference herein.

In other embodiments, the training of the deep learning networks may be performed using training data that is generated as described in related applications U.S. Ser. No. 16/697,146, filed on 26 Nov. 2019, entitled "METHODS AND SYSTEMS FOR GENERATING 3D DATASETS TO TRAIN DEEP LEARNING NETWORKS FOR MEASUREMENTS ESTIMATION," the entire disclosure of which is hereby incorporated by reference herein.

Training Example

A starting point for any machine learning method such as used by the deep learning component above is a documented dataset containing multiple instances of system inputs and correct outcomes (e.g., the training data). This data set can be used, using methods known in the art, including but not limited to standardized machine learning methods such as parametric classification methods, non-parametric methods, decision tree learning, neural networks, methods combining both inductive and analytic learning, and modeling approaches such as regression models, to train the machine learning system and to evaluate and optimize the performance of the trained system. The quality of the output of the machine learning system depends on (a) the pattern parameterization, (b) the learning machine design, and (c) the quality of the training database.

As one example, the segmentation DLN may also be trained on a body segmentation or body feature extraction. In one embodiment, the segmentation DLN may be trained using annotated body segmentation data. For example, the segmentation DLN may be presented with labeled data (e.g., an image of a subject and associated actual body segmentations) and may determine an error function (e.g., from a loss function, as discussed above) based on the results of the segmentation DLN and the actual body segmentation. The segmentation DLN may be trained to reduce the magnitude of the error function.

In another embodiment, the segmentation DLN may be validated by accuracy estimation techniques like a holdout method, which may split the data (e.g., all images including images having corresponding segmentations received from the annotator, and images on which to extract segmentations using the segmentation DLN and having no corresponding segmentations) in a training and test set (conventionally ⅔ training set and ⅓ test set designation) and may evaluate the performance of the segmentation DLN model on the test set. In another embodiment, a N-fold-cross-validation method may be used, where the method randomly splits the data into k subsets where k-1 instances of the data are used to train the segmentation DLN model while the kth instance is used to test the predictive ability of the segmentation DLN model. In addition to the holdout and cross-validation methods, a bootstrap method may be used, which samples n instances with replacement from the dataset, can be used to assess the segmentation DLN model accuracy.

For the annotation step of 205 in FIG. 2, one or more annotation DLNs for each body feature may be trained, or alternatively a single annotation DLN for the entire body may be trained. For example, sixteen annotation DLNs, one for each of 16 different body parts, may be trained. The annotation DLN may be presented with labeled data (e.g., an image of a subject with line annotations or key point annotations) and may determine an error function (e.g., from a loss function, as discussed above) based on the results of the annotation DLN and the actual annotations from the annotator. The annotation DLN may be trained to reduce the magnitude of the error function.

In another embodiment, an annotation DLN may be trained specifically to draw key point annotations for a particular body feature, for example, a specific body part, such as an arm, a leg, a neck, and so on. In another embodiment, the training of the annotation DLN for each body feature may be performed in series (e.g., in a hierarchical manner, with groups of related body features being trained one after the other) or in parallel. In another embodiment, different training data sets may be used for different annotation DLNs, the different annotation DLNs corresponding to different body features or body parts. In one embodiment, there may be more or less than sixteen DLNs for the sixteen body parts, for example, depending on computational resources. In another embodiment, the training of the annotation DLNs may be performed at least partially in the cloud.

Finally, one or more weight ML modules may be trained. In one embodiment, the weight ML module may be trained using received weight measurements. For example, the weight ML module may be presented with labeled data (e.g., a subject feature vector and associated actual weight measurement data received from a scale or a database) and may determine an error function (e.g., from a loss function, as discussed above) based on the results of the weight ML module and the actual received weight measurements. The weight ML module may be trained to reduce the magnitude of the error function.

In another embodiment, one or more weight ML modules may be trained specifically to extract weight measurements from a particular geometric feature, for example, the circumference, area, or volume of a specific body part, such as an arm, a leg, or a neck. In another embodiment, a single weight ML module may be trained specifically to extract a whole body weight measurement from a group of body geometric features. In another embodiment, different training data sets may be used for different weight ML modules, each weight ML module corresponding to different feature vectors (e.g., circumference, image area, and/or volume). In one embodiment, the training of the weight ML modules may be performed at least partially in the cloud, to be described below.

The trained segmentation DLN, annotation DLN, and weight ML module to be used in FIGS. 1-3 may be trained for later use. In particular, the trained segmentation DLN is trained for use in step 204 in FIG. 2. Similarly, the one or more trained annotation DLNs are trained for use in step 205 in FIG. 2. Finally, the trained weight ML module is trained for use in steps 213, 223, and 233 in FIG. 2.

Illustrative Client-Server Implementation

Figure 6:
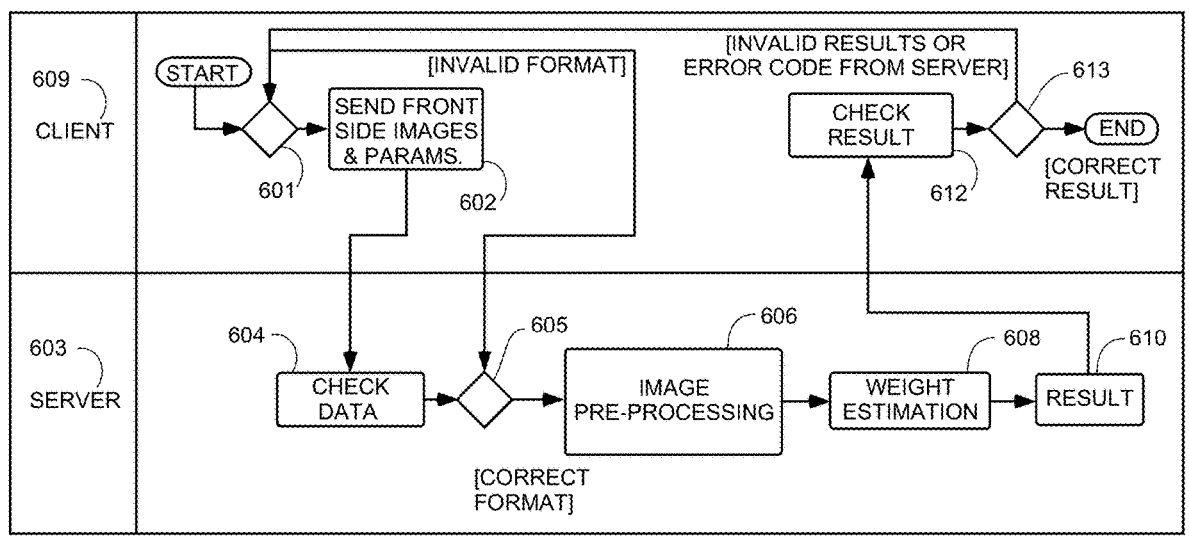
FIG. 6 shows an illustrative client-server diagram for implementing body weight measurement, in accordance with one embodiment of the invention.

FIG. 6 shows an illustrative client-server diagram 600 for implementing body weight prediction, in accordance with one embodiment of the invention. The client-side 609 is shown at the top, while the server-side 603 is shown at the bottom. The client initiates the process by sending front and side images at 602. After receiving the images, the server checks the images for the correctness of the format and other formal checks at 604. If images are not of the correct format or have other formal problems at 605, such as wrong pose, poor contrast, too far or too close, subject not in view, subject partially obstructed, and so forth, the process returns this information to the client at 601. At 601, an error message or other communication may be displayed at the client side, in one embodiment, to enable the user to retake the images.

If the images are of the correct format and have no other formal problems at 605, the images are pre-processed at 606 so that they can be handled by the weight estimation module 608. The images are then processed through the weight estimation module 608 to determine subject weight result 610, as described in greater detail previously. The weight result 610 is returned from the server to the client. The client checks the weight result at 612. If the weight result have any formal problems, for example being out-of-bounds, unreasonably small or large, and so on, as determined at 613, the process returns to 601, and similarly displays an error message or other communication may be displayed to the subject to enable the user to retake the images. If the weight result has no formal problems, as determined at 613, the process ends with the predicted body weight ready for display or use.

It may be appreciated that the image, format correctness, and other formal checks carried out at the server side at step 604 may be carried out at the client side (e.g., as a bandwidth-saving measure). Similarly, the weight result check performed by the client at step 612 may be carried out by the server.

Alternative Architectures: Combining DLNs and/or ML Modules

In some embodiments, the annotation DLN and weight ML may be implemented as one weight DLN, that annotates and performs weight measurements, or may be implemented as two separate modules, an annotation DLN that annotates each body feature, and a separate weight ML module that performs the weight measurements. Similarly, various alternative architectures for implementing the segmentation DLN of step 204, the annotation DLN of step 205, and the weight ML module of steps 213, 223, and 233 are described. For example, FIG. 7 corresponds to the architecture shown in FIG. 2, in which the segmentation DLN, annotation DLN, and weight ML module are separate modules. In contrast, FIG. 1 corresponds to an alternative architecture in which the segmentation DLN and annotation DLN are combined into a single annotation DLN (that effectively performs both segmentation and annotation) followed by a weight ML module. Finally, yet another alternative architecture (not shown) is possible in which the segmentation DLN, annotation DLN, and weight ML module are all combined into a single weight DLN that effectively performs all functions of segmentation, annotation, and weight measurement. These options are discussed in turn.

Figure 7:
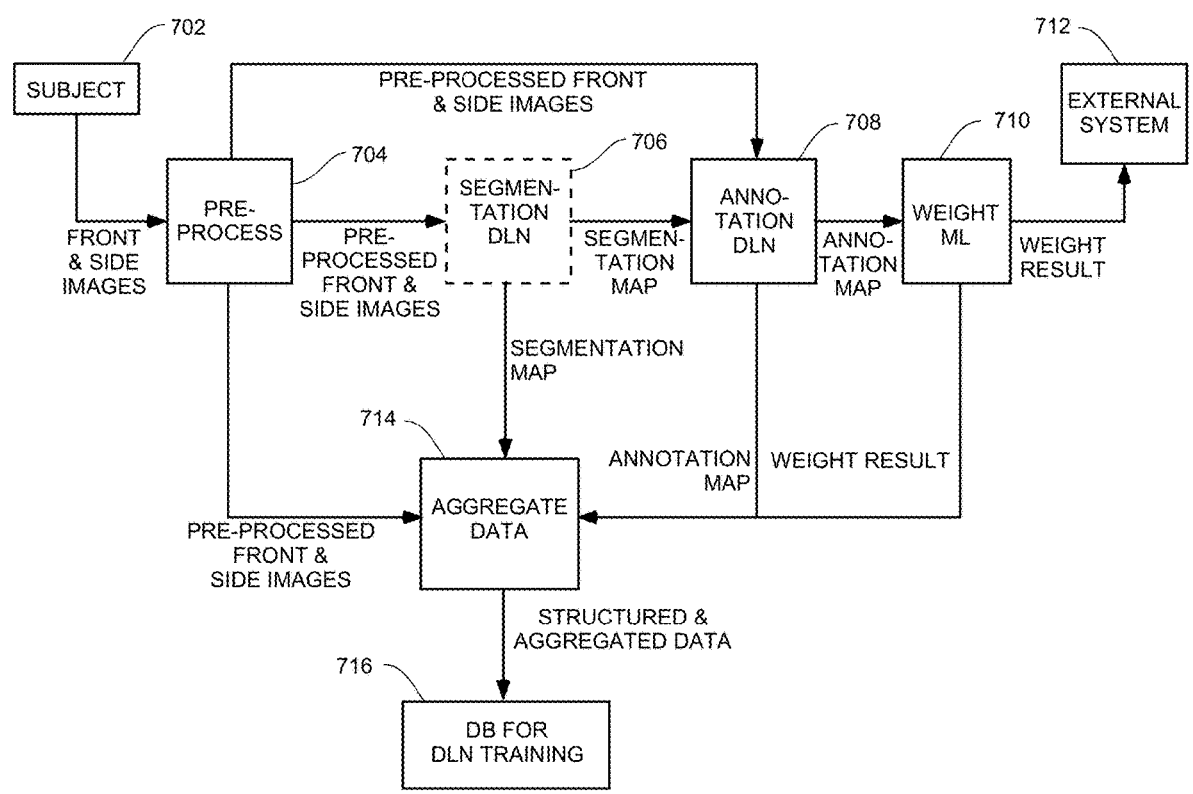
FIG. 7 shows an example flow diagram for body weight determination, showing separate segmentation DLN, annotation DLN, and weight machine learning module, in accordance with one embodiment of the invention.

FIG. 7 shows a diagram of one example flow diagram 700 for body weight prediction (using separate segmentation DLN, annotation DLN, and weight ML modules), in accordance with one embodiment of the invention. In one embodiment, front and side images are received from a subject at 702. The images are pre-processed at 704. As previously discussed, in some embodiments, a pre-processing on the one or more images of the subject, such as a perspective correction, may be performed on the front and side view photos, if needed. Various computer vision techniques may be utilized to further pre-process the one or more images. Examples of further pre-processing steps may include contrast, lighting, and other image processing techniques to improve the quality of the one or more images before further processing.

After pre-processing, the pre-processed images are sent to the segmentation DLN at 706 to generate the segmentation map, as discussed previously. The segmentation map is aggregated with the rest of the data at 714. In parallel to the segmentation, in one embodiment, the pre-processed images are also sent to annotation DLN at 708 to generate the annotation key points, as discussed previously. The annotation map is aggregated with the rest of the data at 714. The annotation map is provided, in one embodiment, to weight machine learning (ML) module 710 to calculate the geometric feature for each body part that has been segmented and annotated based on the annotation key points, as discussed previously. The weight result is aggregated with the rest of the data at 714. The weight result is output to one or more external system(s) for various uses as described herein at 712. Finally, all of the aggregated and structured data, (1) the pre-processed front and side images, (2) the segmentation map, (3) the annotation map, and (4) the weight result, that have been aggregated at 714 are stored in a database for further DLN training at 716.

In another embodiment, step 706 is optional, and body feature identification is carried out in step 708, and step 714 requires only the output annotation map (e.g., annotation key points) from step 708. In accordance with this embodiment of the invention, body weight measurement determination can be carried out using a combined segmentation-annotation DLN and weight ML module. Front and side images are received from a subject 702 and pre-processed 704 as previously discussed. After pre-processing, the pre-processed images are sent directly to the annotation DLN 708 to generate the annotation map, as discussed previously. Instead of first performing body feature segmentation 706, in this alternative embodiment, the annotation key points are drawn directly on the images without explicitly segmenting the body features from the background, using a specially-trained combined segmentation-annotation DLN that effectively combines the functions of both the segmentation DLN 706 and the annotation DLN 708 (shown in the embodiment in FIG. 7) into a single annotation DLN. In effect, the body feature segmentation is performed implicitly by the annotation DLN 708.

In yet another embodiment, the annotation DLN 708 and weight ML 710 can be further combined. Front and side images are received from a user at 702, and the images are pre-processed at 704, as previously discussed. After pre-processing, the pre-processed images are sent directly to the weight DLN at 710 to generate the complete body weight prediction, as discussed previously. Instead of first performing body feature segmentation and annotation, in this alternative embodiment, the body weight is directly extracted from the pre-processed images without explicitly segmenting the body features from the background (and without explicitly drawing the key point annotations) using a specially-trained weight DLN that effectively combines the features of the segmentation DLN, the annotation DLN, and the weight ML modules into a single weight DLN (not shown in FIG. 7). In effect, the body feature segmentation and annotation is performed implicitly by the weight DLN in one or more of its neural network layers.

Hardware, Software, and Cloud Implementations

As discussed, the data (e.g., photos, textual descriptions, and the like) described throughout the disclosure can include data that is stored on a database stored or hosted on a cloud computing platform. It is to be understood that although this disclosure includes a detailed description on cloud computing, below, implementation of the teachings recited herein are not limited to a cloud computing environment. Rather, embodiments of the present invention are capable of being implemented in conjunction with any other type of computing environment now known or later developed.

Cloud computing can refer to a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. A cloud computing environment is service oriented with a focus on statelessness, low coupling, modularity, and semantic interoperability. At the heart of cloud computing is an infrastructure that includes a network of interconnected nodes.

The cloud computing environment may include one or more cloud computing nodes with which local computing devices used by cloud consumers, such as, for example, personal digital assistant (PDA) or cellular telephone, desktop computer, laptop computer, and/or automobile computer system can communicate. Nodes can communicate with one another. They can be group physically or virtually, in one or more networks, such as private, community, public, or hybrid clouds, or a combination thereof. This allows cloud computing environment to offer infrastructure, platforms and/or software as services for which a cloud consumer does not need to maintain resources on a local computing device. It is understood that the types of computing devices are intended to be exemplary only and that computing nodes and cloud computing environment can communicate with any type of computerized device over any type of network and/or network addressable connection (e.g., using a web browser).

Figure 8:
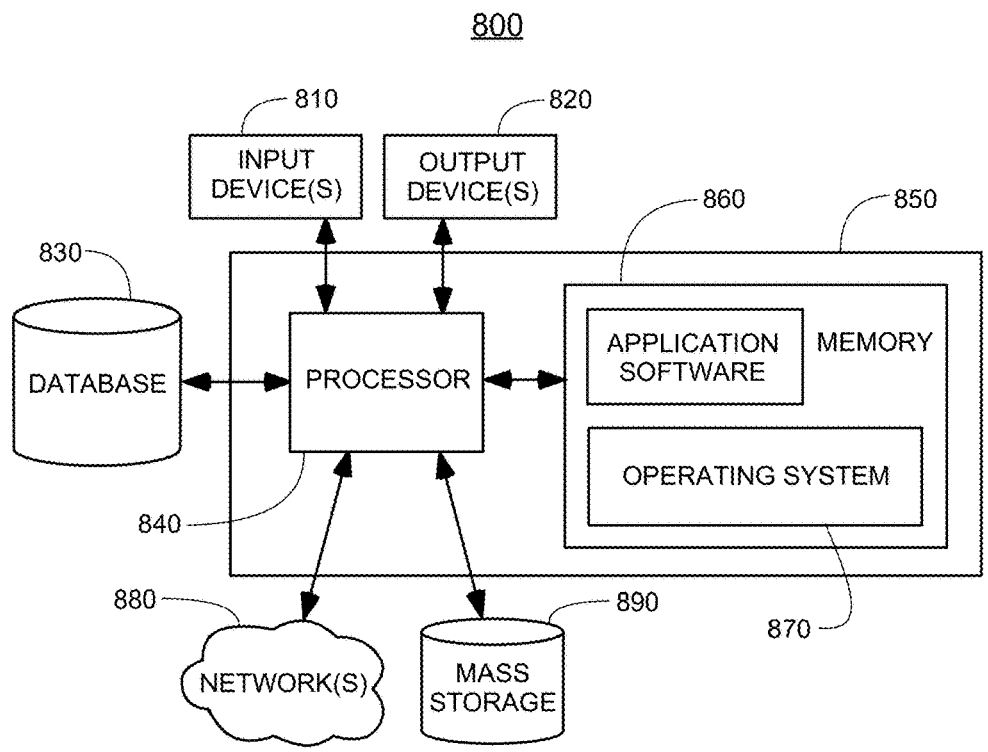
FIG. 8 shows an illustrative hardware architecture diagram of a server for implementing one embodiment of the present invention.

FIG. 8 shows an illustrative hardware architecture diagram of a server for implementing one embodiment of the present invention. Many components of the system, for example, network interfaces etc., have not been shown, so as not to obscure the present invention. However, one of ordinary skill in the art would appreciate that the system necessarily includes these components. A user-device is a hardware that includes at least one processor 840 coupled to a memory 850. The processor may represent one or more processors (e.g., microprocessors), and the memory may represent random access memory (RAM) devices comprising a main storage of the hardware, as well as any supplemental levels of memory e.g., cache memories, non-volatile or back-up memories (e.g. programmable or flash memories), read-only memories, etc. In addition, the memory may be considered to include memory storage physically located elsewhere in the hardware, e.g. any cache memory in the processor, as well as any storage capacity used as a virtual memory, e.g., as stored on a mass storage device.

The hardware of a user-device also typically receives a number of inputs 810 and outputs 820 for communicating information externally. For interface with a user, the hardware may include one or more user input devices (e.g., a keyboard, a mouse, a scanner, a microphone, a web camera, etc.) and a display (e.g., a Liquid Crystal Display (LCD) panel). For additional storage, the hardware my also include one or more mass storage devices 890, e.g., a floppy or other removable disk drive, a hard disk drive, a Direct Access Storage Device (DASD), an optical drive (e.g. a Compact Disk (CD) drive, a Digital Versatile Disk (DVD) drive, etc.) and/or a tape drive, among others. Furthermore, the hardware may include an interface one or more external databases 830, as well as one or more networks 880 (e.g., a local area network (LAN), a wide area network (WAN), a wireless network, and/or the Internet among others) to permit the communication of information with other computers coupled to the networks. It should be appreciated that the hardware typically includes suitable analog and/or digital interfaces to communicate with each other.

The hardware operates under the control of an operating system 870, and executes various computer software applications 860, components, programs, codes, libraries, objects, modules, etc. indicated collectively by reference numerals to perform the methods, processes, and techniques described above.

Figure 9:
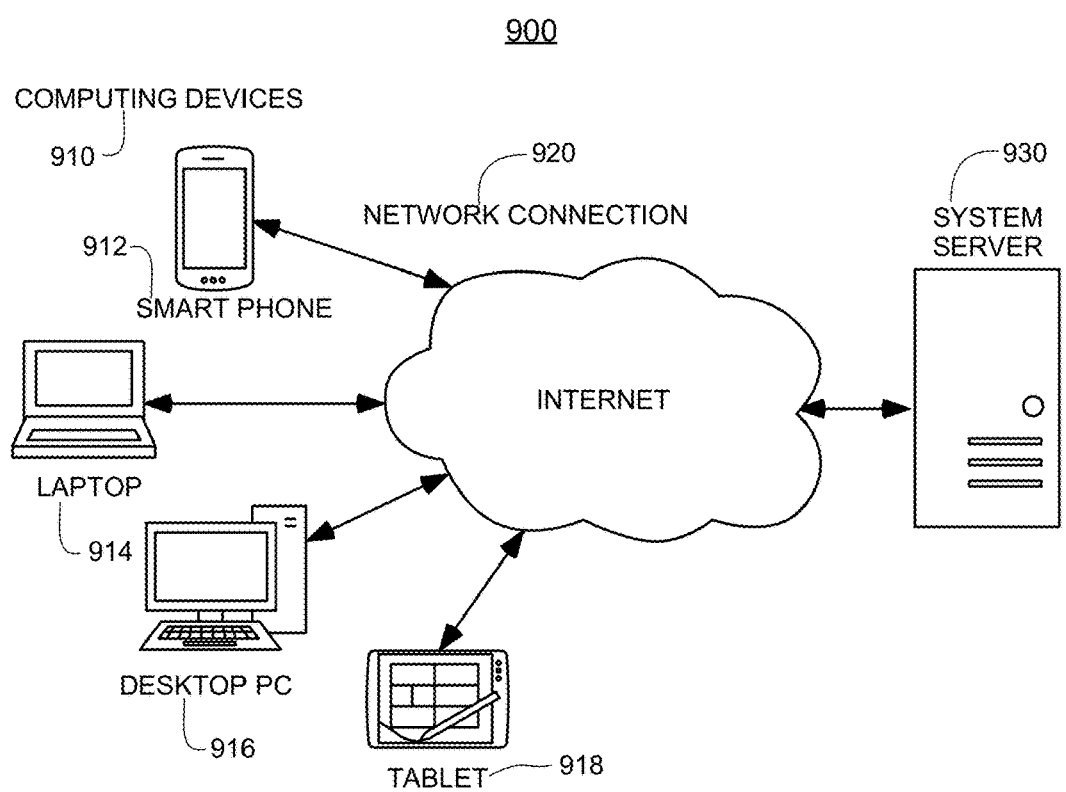
FIG. 9 shows an illustrative system architecture diagram for implementing one embodiment of the present invention in a client server environment.

FIG. 9 shows an illustrative system architecture for implementing one embodiment of the present invention in a client server environment. Computing devices 910 on the client side may include smart phones 912, laptops 914, desktop PCs 916, tablets 918, or other devices. Such computing devices 910 access the service of the system server 930 through some network connection 920, such as the Internet. As discussed, the entire system can be implemented and offered to the end-users and operators over the Internet, in a so-called cloud implementation. No local installation of software or hardware would be needed, and the end-users and operators would be allowed access to the systems of the present invention directly over the Internet, using either a web browser or similar software on a client, which client could be a desktop, laptop, mobile device, and so on. This eliminates any need for custom software installation on the client side and increases the flexibility of delivery of the service (software-as-a-service), and increases user satisfaction and ease of use. Various business models, revenue models, and delivery mechanisms for the present invention are envisioned, and are all to be considered within the scope of the present invention.

In general, the method executed to implement the embodiments of the invention, may be implemented as part of an operating system or a specific application, component, program, object, module or sequence of instructions referred to as "computer program(s)" or "computer code(s)." The computer programs typically comprise one or more instructions set at various times in various memory and storage devices in a computer, and that, when read and executed by one or more processors in a computer, cause the computer to perform operations necessary to execute elements involving the various aspects of the invention. Moreover, while the invention has been described in the context of fully functioning computers and computer systems, those skilled in the art will appreciate that the various embodiments of the invention are capable of being distributed as a program product in a variety of forms, and that the invention applies equally regardless of the particular type of machine or computer-readable media used to actually effect the distribution. Examples of computer-readable media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), and digital and analog communication media.

Example Use Cases of the Present Invention

Figures 10, 11:
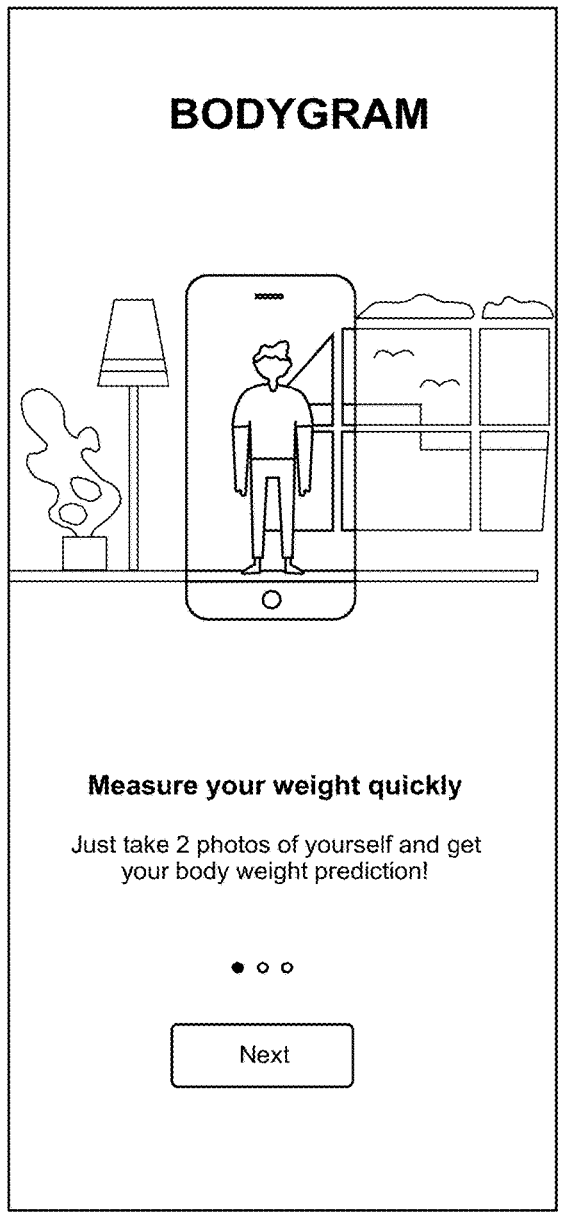
FIG. 10 shows an illustrative diagram of a use case of the present invention in which a mobile device with a single camera is used to measure human body weight, showing a graphical user interface (GUI) with user instructions for capturing photos of the subject, according to one embodiment of the present invention.
FIG. 11 shows an illustrative diagram of the mobile device GUI for receiving one or more subject parameters, according to one embodiment of the present invention.

FIGS. 10-17 show illustrative diagrams of a use case of the present invention in which a mobile device with a single camera is used to measure human body weight, showing mobile graphical user interfaces (GUIs) in which some embodiments of the present invention have been implemented. FIG. 10 shows an illustrative diagram of the mobile device GUI showing user instructions for capturing a front view photo. FIG. 11 shows an illustrative diagram of the mobile device GUI for receiving one or more subject parameters. For example, FIG. 11 shows a GUI screen for receiving the subject's height via input from the user. Although people do not have an accurate estimate of their own weight, nearly all adult people know their own height to a high degree of accuracy. As discussed, the height of the subject is used as normalization data for measuring a geometric feature (e.g., the circumferences of the subject's body parts) in real-world coordinates from the pixel measurements. The GUI screen in FIG. 11 may also receive other subject parameters, such as gender, age, and ethnicity. For example, the GUI screen of FIG. 11 shows a drop-down menu and radio buttons for this purpose.

Figure 12:
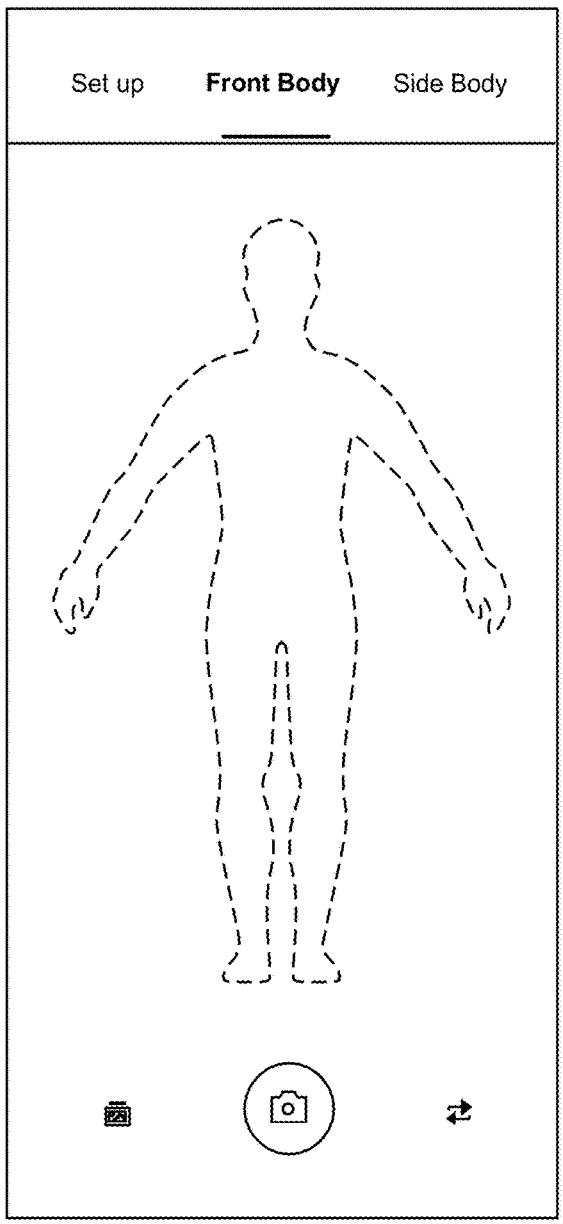
FIG. 12 shows an illustrative diagram of the mobile device GUI for capturing the front view photo showing a template indicating where the subject should stand, according to one embodiment of the present invention.
Figure 13:
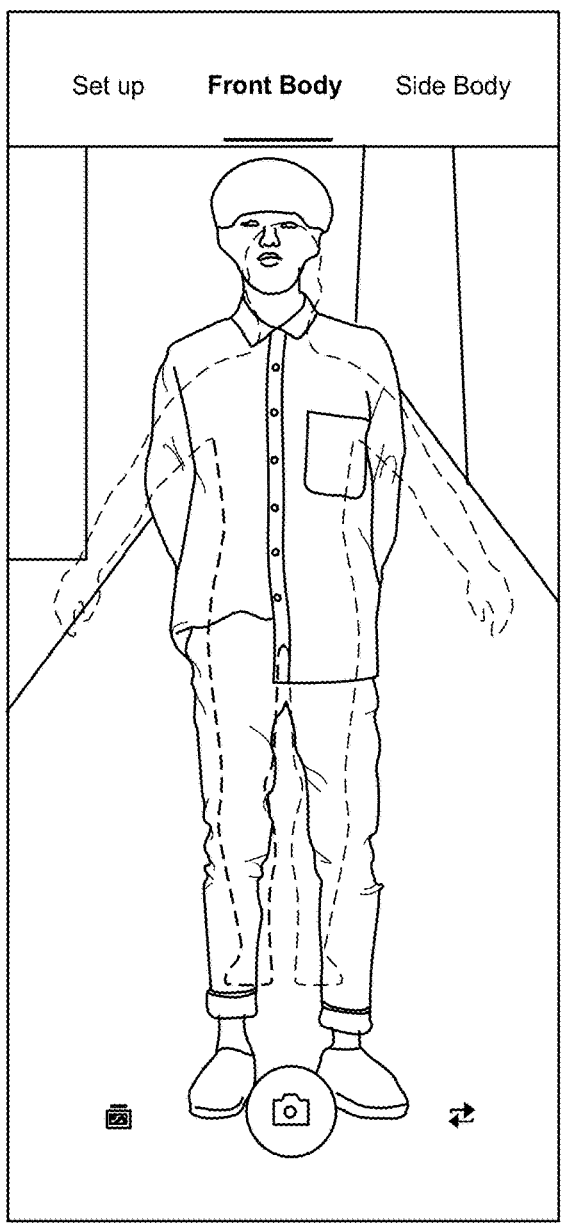
FIG. 13 shows another illustrative diagram of the mobile device GUI for capturing the front view photo showing the template indicating where the subject should stand overlaid in augmented reality over an image of the subject, according to one embodiment of the present invention.
Figure 14:
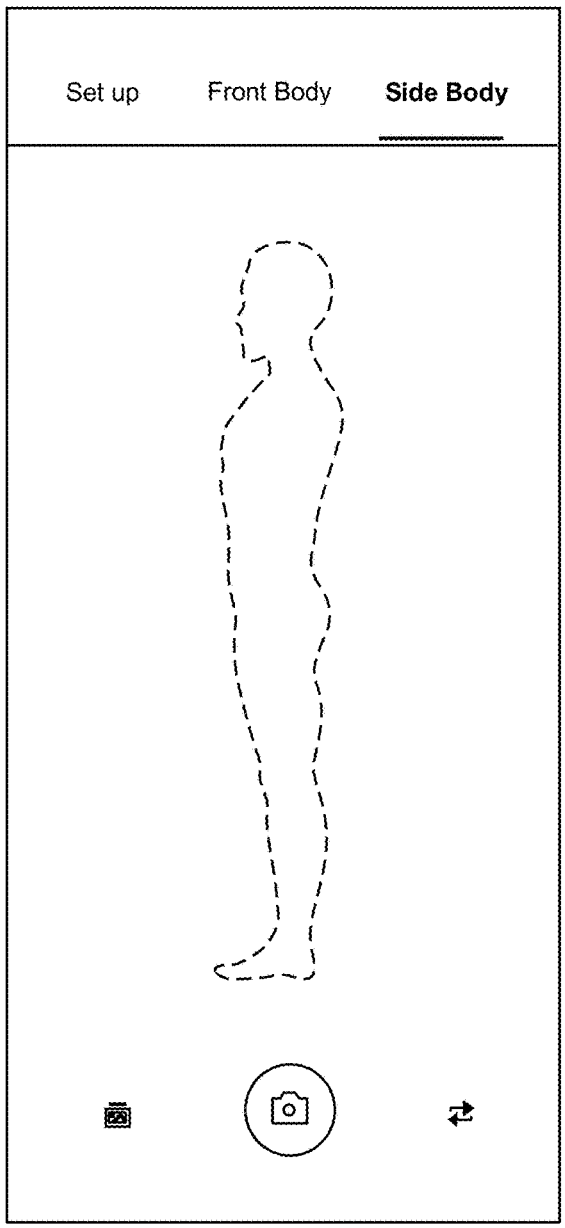
FIG. 14 shows an illustrative diagram of the mobile device GUI for capturing the side view photo, according to one embodiment of the present invention.
Figure 15:
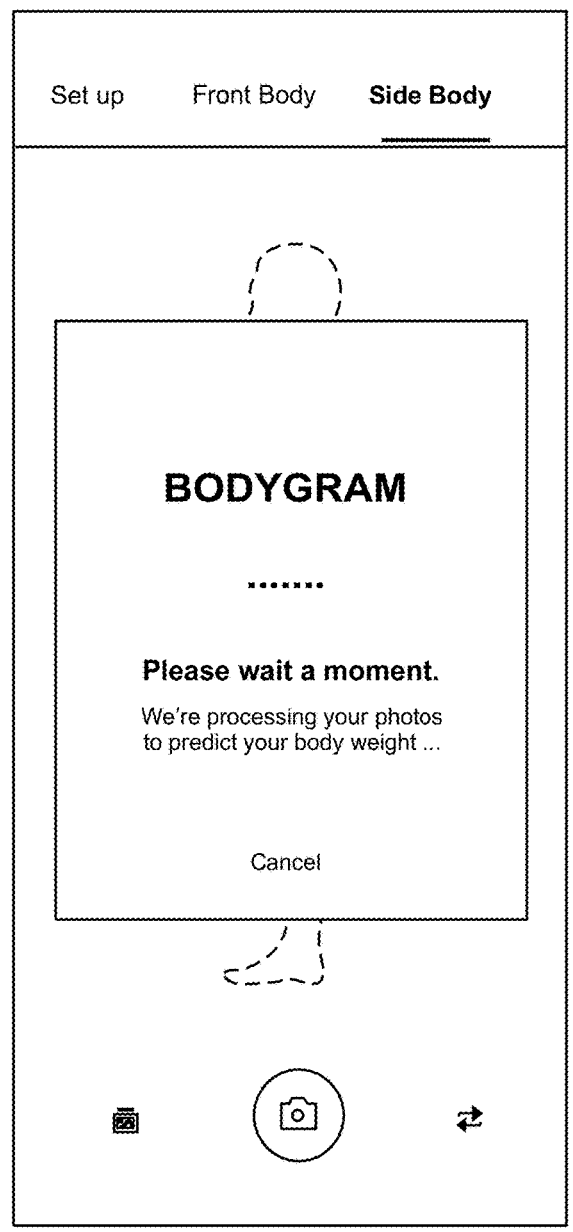
FIG. 15 shows an illustrative diagram of the mobile device GUI that is displayed while the system processes the captured photos to predict the body weight, according to one embodiment of the present invention.
Figure 16:
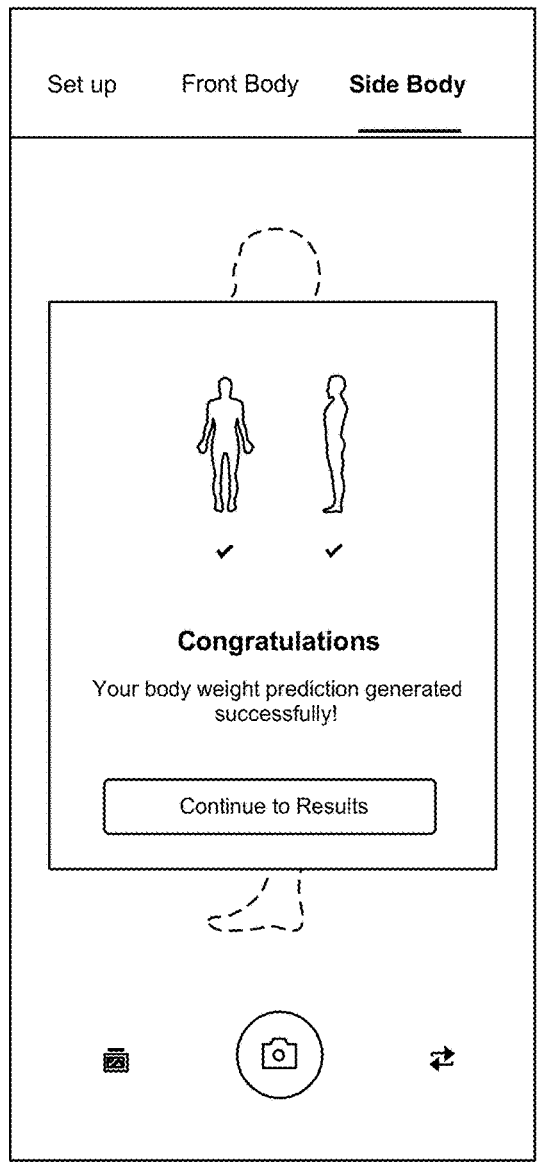
FIG. 16 shows an illustrative diagram of the mobile device GUI showing a notification screen when the body weight prediction has been successfully completed, according to one embodiment of the present invention.

FIG. 12 shows an illustrative diagram of the mobile device GUI for capturing the front view photo. FIG. 13 shows another illustrative diagram of the mobile device GUI for capturing the front view photo, with an illustrative A-pose overlaid in augmented reality (AR) on the mobile device GUI over the real-time image of the subject. FIG. 14 shows an illustrative diagram of the mobile device GUI for capturing the side view photo. FIG. 15 shows an illustrative diagram of the mobile device GUI that is displayed while the system processes the photos to predict the body weight. Finally, FIG. 16 shows an illustrative diagram of the mobile device GUI showing a notification screen when the body weight prediction has been successfully completed.

Figure 17:
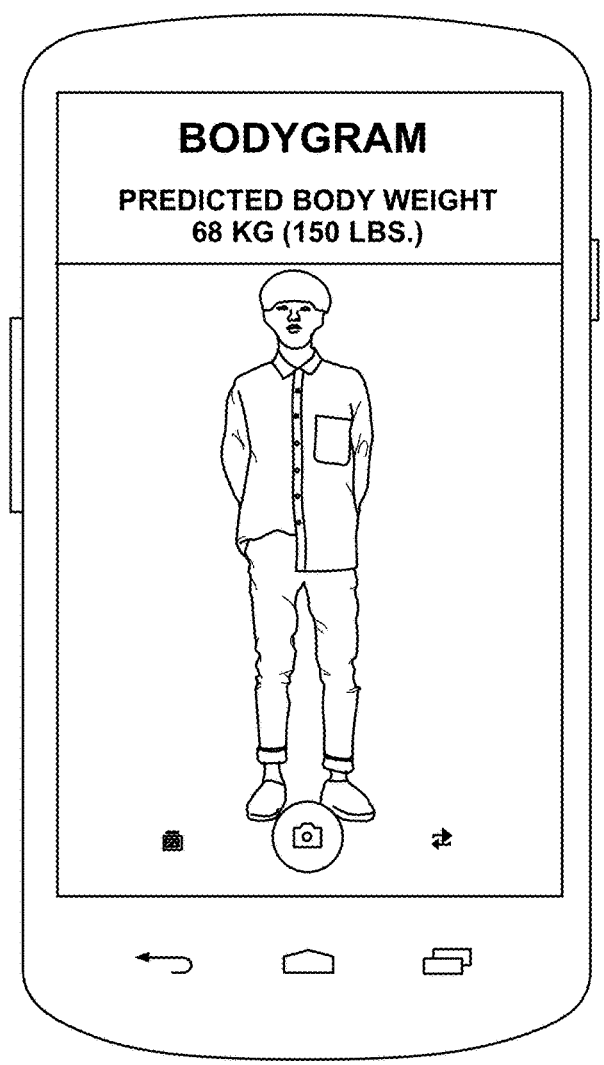
FIG. 17 shows an illustrative diagram of the mobile device used to predict body weight from user photos, showing the mobile device GUI with a notification screen when the body weight prediction has been successfully completed, according to one embodiment of the present invention.

FIG. 17 is an illustrative diagram of a use case of the present invention in which a single camera on a mobile device is used to measure human body weight, showing a front view of a human in typical clothing standing against a normal background. The mobile device shown in FIG. 17 comprises at least one camera, a processor, a non-transitory storage medium, and a wireless communication to a server (not shown). In one embodiment, the hardware architecture of the mobile device and the server are as shown in FIG. 8. In one embodiment, the one or more photos of the subject's body are transmitted to a server that performs the operations described herein. In one embodiment, the one or more photos of the subject's body are analyzed locally by the processor of the mobile device. The operations performed return one or more body weight predictions, which may be stored on the server, as well as presented to the user, as shown in FIG. 17. In addition, the body weight predictions may then be utilized for many purposes, including but not limited to, offering for sale to the subject one or more custom garments, custom body suites, custom PPE (personal protection equipment), custom diet regiments, custom exercise, gym, or workout routines, and so on. Further, the body weight predictions may be output to a third-party mobile device and/or a third-party server. In one embodiment, the output may be in the form of a text message, an email, a textual description on a mobile application or website, combinations thereof, and the like.

Without loss of generality, the body weight predictions may be output, transmitted, and/or utilized for any purpose for which body weight is useful. In particular, the body weight predictions may be output to a computing device and/or a corresponding server, for example associated with a company that recommends exercise, fitness, or diet regimens based on the weight measurement. One of ordinary skill in the art would recognize that the output of the body weight measurements may be utilized for any purpose in which accurate and simple body weight measurements are useful, such as but not limited to fitness, health, shopping, and so forth.

In conclusion, the present invention is able to use just two photos and achieve accuracy in body weight measurement comparable to a standard weight scale. The system does not require the use of any specialized hardware sensors, does not require the user to stand against any special background, does not require special lighting, can be used with photos taken at any distance, and with the user wearing any type of clothing. The result is a body weight measurement system that works with any mobile device so that anyone can easily take photos of themselves and benefit from automatic body weight measurement.

One of ordinary skill in the art knows that the use cases, structures, schematics, and flow diagrams may be performed in other orders or combinations, but the inventive concept of the present invention remains without departing from the broader scope of the invention. Every embodiment may be unique, and methods/steps may be either shortened or lengthened, overlapped with the other activities, postponed, delayed, and continued after a time gap, such that every user is accommodated to practice the methods of the present invention.

Although the present invention has been described with reference to specific exemplary embodiments, it will be evident that the various modification and changes can be made to these embodiments without departing from the broader scope of the invention. Accordingly, the specification and drawings are to be regarded in an illustrative sense rather than in a restrictive sense. It will also be apparent to the skilled artisan that the embodiments described above are specific examples of a single broader invention which may have greater scope than any of the singular descriptions taught. There may be many alterations made in the descriptions without departing from the scope of the present invention.

What is claimed is:

1. A computer-implemented method for predicting a body weight of a subject, the computer-implemented method executable by a hardware processor, the method comprising:
   receiving one or more subject parameters;
   receiving one or more images containing the subject;
   identifying one or more annotation key points for one or more body parts underneath a clothing of the subject from the one or more images utilizing an annotation deep-learning module;
   calculating one or more geometric features of the subject based on the one or more annotation key points; and
   generating a prediction of the body weight of the subject utilizing a weight machine-learning module based on a feature vector comprising the one or more geometric features of the subject and the one or more subject parameters,
   wherein the weight machine-learning module predicts the body weight of the subject from the one or more subject parameters and the one or more geometric features calculated from the one or more annotation key points from the annotation deep-learning module, and
   wherein the weight machine-learning module was trained on ground truth data comprising one or more sample body weights and one or more sample feature vectors for one or more sample subjects.

2. The method of claim 1, wherein the one or more geometric features are selected from the group consisting of body part circumference(s), body part length(s), body image area(s), body part image area(s), body volume(s), and body part volume(s).

3. The method of claim 2, wherein the body part circumference(s) comprise multiple body part circumferences for at least one body part.

4. The method of claim 1, wherein the generating the prediction of the body weight of the subject further comprises:
   generating the feature vector comprising the one or more geometric features and the one or more subject parameters as input to the weight machine-learning module.

5. The method of claim 4, wherein the weight machine-learning module comprises one or more of a linear regressor, a nonlinear regressor, and a random forest algorithm.

6. The method of claim 1, wherein one or more of the subject parameters are used as normalization data to scale from pixel coordinates to real-world coordinates in the one or more images.

7. The method of claim 6, wherein a height of the subject is used as the normalization data.

8. The method of claim 1, wherein the one or more images comprises at least two images, and wherein the at least two images contain the subject in at least two perspective views.

9. The method of claim 8, wherein the at least two images comprise at least a front-view image and a side-view image of the subject, and
   wherein the generating the one or more geometric features based on the one or more annotation key points comprises one step selected from the group consisting of:
   (a) calculating at least one circumference of at least one annotated body part utilizing annotated front-view and side-view images and a height of the subject;
   (b) calculating at least one body part image area of at least one annotated body part utilizing annotated front-view and side-view images and a height of the subject; and
   (c) calculating at least one body part volume of at least one annotated body part utilizing annotated front-view and side-view images and a height of the subject.

10. The method of claim 1, further comprising the following steps after the receiving the one or more images:
    performing body segmentation on the images to identify the one or more body parts associated with the subject from a background,
    wherein the body segmentation utilizes a segmentation deep-learning module that has been trained on segmentation training data, and wherein the segmentation training data comprise one or more images for one or more sample subjects and a body part segmentation for each body part for the one or more sample subjects.

11. The method of claim 1, wherein the annotation deep-learning modules utilize training data comprising one or more images for one or more sample subjects and one or more annotation key points for each body part for the one or more sample subjects.

12. The method of claim 1, wherein the one or more subject parameters are selected from the group consisting of a height, a received subject weight estimate, a gender, an age, an ethnicity, and a demographic information associated with the subject.

13. The method of claim 1, wherein the prediction of the body weight of the subject is a first estimate, and wherein the method further comprises:
generating a second estimate of the body weight of the subject using a second machine-learning module;
comparing a first confidence score of the first estimate and a second confidence score of the second estimate; and
selecting either the first estimate or the second estimate as the body weight of the subject based on the first and the second confidence scores.

14. The method of claim 1, further comprising:
determining whether the prediction of the body weight of the subject corresponds to a confidence level below a predetermined value; and
in response to determining that the prediction of the body weight of the subject corresponds to a confidence level below the predetermined value,
comparing the prediction of the body weight of the subject to a received subject weight estimate,
updating the prediction of the body weight of the subject, wherein the received subject weight estimate is used to guide the weight machine-learning module, and
replacing the prediction of the body weight of the subject with an updated prediction of the body weight of the subject.

15. The method of claim 1, wherein the one or more subject parameters are received from a mobile computing device, and wherein the images of the subject are received from a camera on the mobile computing device.

16. The method of claim 15, wherein the one or more subject parameters received from the mobile computing device comprises receiving a measurement performed by the mobile computing device.

17. The method of claim 15, wherein a depth data from a depth sensor on the mobile computing device is used as normalization data to scale from pixel coordinates to real-world coordinates in the one or more images.

18. The method of claim 15, further comprising:
pre-processing the one or more images of the subject and a background before identifying the annotation key points,
wherein the pre-processing comprises at least a perspective correction on the one or more images, and
wherein the perspective correction is selected from the group consisting of perspective correction utilizing a head of the subject, perspective correction utilizing a gyroscope of the mobile computing device, and a perspective correction utilizing another sensor of the mobile computing device.

19. A computer program product for predicting a body weight of a subject, comprising a non-transitory computer readable storage medium having program instructions embodied therein, the program instructions executable by a processor to cause the processor to:
receive one or more subject parameters;
receive one or more images containing the subject;
identify one or more annotation key points for one or more body parts underneath a clothing of the subject from the one or more images utilizing an annotation deep-learning modules;
calculate one or more geometric features of the subject based on the one or more annotation key points; and
generate a prediction of the body weight of the subject utilizing a weight machine-learning module based on a feature vector comprising the one or more geometric features of the subject and the one or more subject parameters,
wherein the weight machine-learning module predicts the body weight of the subject from the one or more subject parameters and the one or more geometric features calculated from the one or more annotation key points from the annotation deep-learning module, and
wherein the weight machine-learning module was trained on ground truth data comprising one or more sample body weights and one or more sample feature vectors for one or more sample subjects.

20. The computer program product of claim 19, wherein the one or more geometric features are selected from the group consisting of body part circumference(s), body part length(s), body image area(s), body part image area(s), body volume(s), and body part volume(s).

* * * * *